US 6,663,820 B2

(12) United States Patent
Arias et al.

(10) Patent No.: US 6,663,820 B2
(45) Date of Patent: Dec. 16, 2003

(54) METHOD OF MANUFACTURING MICRONEEDLE STRUCTURES USING SOFT LITHOGRAPHY AND PHOTOLITHOGRAPHY

(75) Inventors: Francisco Arias, Cincinnati, OH (US); Faiz Feisal Sherman, West Chester, OH (US); Grover David Owens, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 48 days.

(21) Appl. No.: 09/808,534

(22) Filed: Mar. 14, 2001

(65) Prior Publication Data

US 2002/0133129 A1 Sep. 19, 2002

(51) Int. Cl.$^7$ .......................... B29C 35/08; B29C 33/40
(52) U.S. Cl. ..................... 264/496; 264/225; 264/319
(58) Field of Search ................. 264/400, 482, 264/496, 219, 154, 322, 227, 225, 319; 205/70, 164; 216/11, 41

(56) References Cited

U.S. PATENT DOCUMENTS

| 3,918,449 A | 11/1975 | Pistor |
| 3,964,482 A | 6/1976 | Gerstel et al. |
| 4,055,029 A | 10/1977 | Kalbow |
| 4,180,232 A | 12/1979 | Hardigg |
| 4,381,963 A | 5/1983 | Goldstein et al. |
| 4,585,991 A | 4/1986 | Reid et al. |
| 4,784,737 A | 11/1988 | Ray et al. |
| 4,837,049 A | 6/1989 | Byers et al. |

(List continued on next page.)

FOREIGN PATENT DOCUMENTS

| DE | 2319591 | 11/1974 |
| DE | 196 24 578 A1 | 1/1998 |
| EP | 0 312 662 A1 | 4/1989 |
| EP | 0 407 063 A1 | 1/1991 |
| EP | 0 796 128 B1 | 11/1995 |
| EP | 1 086 719 A1 | 3/2001 |
| EP | 1 174 078 A2 | 1/2002 |
| FR | 2535602 A1 | 11/1984 |

(List continued on next page.)

OTHER PUBLICATIONS

McAllister, H., "Micromachined Microneedles for Transdermal Drug Delivery", Allen & Prausnitz, Georgia Institute of Technology, Atlanta, GA.

Sebastian, H. et al., "Microfabricated Microneedles: A Novel Approach to Transdermal Drug Delivery", Journal of Pharmaceutical Sciences, Aug., 1998, pp. 922–925, vol. 87, No. 8, Atlanta, GA.

Chun, K. et al., An Array of Hollow Microcapillaries for the Controlled Injection of Genetic Materials into Animal/Plat Cells, The University of Tokyo.

(List continued on next page.)

*Primary Examiner*—Mathieu D. Vargot
(74) *Attorney, Agent, or Firm*—Bart S. Hersko

(57) ABSTRACT

A method for manufacturing microneedle structures is disclosed using soft lithography and photolithography, in which micromold structures made of a photoresist material or PDMS are created. The micromold manufacturing occurs quite quickly, using inexpensive materials and processes. Once the molds are available, using moldable materials such as polymers, microneedle arrays can be molded or embossed in relatively fast procedures. In some cases a sacrificial layer is provided between the forming micromold and its substrate layer, for ease of separation. The microneedles themselves can be solid projections, hollow "microtubes," or shallow "microcups." Electrodes can be formed on the microneedle arrays, including individual electrodes per hollow microtube.

7 Claims, 19 Drawing Sheets

U.S. PATENT DOCUMENTS

| | | |
|---|---|---|
| 5,134,079 A | 7/1992 | Cusack et al. |
| 5,156,591 A | 10/1992 | Gross et al. |
| 5,162,043 A | 11/1992 | Lew et al. |
| 5,198,192 A | 3/1993 | Saito et al. |
| 5,215,088 A | 6/1993 | Normann |
| 5,250,023 A | 10/1993 | Lee et al. |
| 5,256,360 A | 10/1993 | Li |
| 5,279,544 A | 1/1994 | Gross et al. |
| 5,318,557 A | 6/1994 | Gross |
| 5,362,307 A | 11/1994 | Guy et al. |
| 5,383,512 A | 1/1995 | Jarvis |
| 5,498,235 A | 3/1996 | Flower |
| 5,527,288 A | 6/1996 | Gross et al. |
| 5,551,953 A | 9/1996 | Lattin et al. |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,676,850 A | 10/1997 | Reed et al. |
| 5,681,580 A | 10/1997 | Jang et al. |
| 5,704,520 A | 1/1998 | Gross |
| 5,711,761 A | 1/1998 | Untereker et al. |
| 5,730,714 A | 3/1998 | Guy et al. |
| 5,735,273 A | 4/1998 | Kurnik et al. |
| 5,771,890 A | 6/1998 | Tamada |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,848,985 A | 12/1998 | Muroki |
| 5,848,990 A | 12/1998 | Cirelli et al. |
| 5,848,991 A | 12/1998 | Gross et al. |
| 5,855,801 A | 1/1999 | Lin et al. |
| 5,879,326 A | 3/1999 | Godshall et al. |
| 5,948,488 A | 9/1999 | Marecki et al. |
| 5,964,729 A | 10/1999 | Choi et al. |
| 6,023,629 A | 2/2000 | Tamada |
| 6,036,659 A | 3/2000 | Ray et al. |
| 6,038,465 A | 3/2000 | Melton, Jr. |
| 6,047,208 A | 4/2000 | Flower |
| 6,083,196 A | 7/2000 | Trautman et al. |
| 6,091,975 A | 7/2000 | Daddona et al. |
| 6,106,751 A | 8/2000 | Talbot et al. |
| 6,129,696 A | 10/2000 | Sibalis |
| 6,132,755 A | 10/2000 | Eicher et al. |
| 6,219,574 B1 | 4/2001 | Cormier et al. |
| 6,256,533 B1 | 7/2001 | Yuzhakov et al. |
| 6,312,612 B1 | 11/2001 | Sherman et al. |
| 6,334,856 B1 | 1/2002 | Allen et al. |
| 6,375,627 B1 | 4/2002 | Mauze et al. |
| 6,379,324 B1 | 4/2002 | Gartstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,494,830 B1 | 12/2002 | Wessel |
| 2001/0023324 A1 | 9/2001 | Pronovost et al. |
| 2002/0006355 A1 | 1/2002 | Whitson |

FOREIGN PATENT DOCUMENTS

| | | |
|---|---|---|
| GB | 783479 | 9/1957 |
| GB | 2221394 A | 2/1990 |
| JP | 09051878 A61 B | 2/1997 |
| SU | 1667864 A6 | 7/1991 |
| WO | WO 93/17754 A1 | 9/1993 |
| WO | WO 94/23777 A1 | 10/1994 |
| WO | WO 95/33612 A1 | 12/1995 |
| WO | WO 96/00109 A1 | 1/1996 |
| WO | WO 96/37155 A1 | 11/1996 |
| WO | WO 96/37256 A1 | 11/1996 |
| WO | WO 97/03718 A1 | 2/1997 |
| WO | WO 97/48440 A1 | 12/1997 |
| WO | WO 97/48441 A1 | 12/1997 |
| WO | WO 97/48442 A1 | 12/1997 |
| WO | WO 98/00193 A1 | 1/1998 |
| WO | WO 99/00155 A1 | 1/1999 |
| WO | WO 99/29298 A2 | 6/1999 |
| WO | WO 99/29364 A1 | 6/1999 |
| WO | WO 99/29365 A1 | 6/1999 |
| WO | WO 99/64580 A1 | 12/1999 |
| WO | WO 00/05166 A1 | 2/2000 |
| WO | WO 00/35530 A1 | 6/2000 |
| WO | WO 00/74763 A2 | 12/2000 |
| WO | WO 00/74766 A1 | 12/2000 |
| WO | WO 02/07813 A1 | 1/2002 |
| WO | WO 02/32331 A2 | 4/2002 |

OTHER PUBLICATIONS

Wouters, S. et al., "Microelectrochemical Systems for Drug Delivery", Electrochimica Acta., 1997, pp. 3385–3390, vol. 42, Nos. 20–22.

Prausnitz, M. R., et al., "Transdermal Delivery of Macromolecules: Recent Advances by Modification of Skin's Barrier Properties", Therapeutic Protein and Peptide Formulation and Delivery, pp. 124–153, Chapter 8, ACS Symposium Series 675, Georgia Institute of Technology.

Prausnitz, M. R., et al., Transdermal Transport Efficiency During Skin Electroporation and Iontophoresis, Journal of Controlled Release 38, 1996, pp. 205–217, Massachusetts Institute of Technology, Cambridge, MA.

Papautsky, I. E., et al., "Micromachined Pipette Arrays (MPA)", pp. 2281–2284, Proceedings—$19^{th}$ International Conference—IEEE/EMBS Oct. 30–Nov. 2, 1997, Chicago, IL.

METHOD OF MANUFACTURING MICRONEEDLE STRUCTURES USING SOFT LITHOGRAPHY AND PHOTOLITHOGRAPHY

TECHNICAL FIELD

The present invention relates generally to microneedle arrays and is particularly directed to a method for manufacturing microneedle structures using soft lithography and photolithography. The invention is specifically disclosed as a method of manufacturing microneedles by creating micromold structures made of a photoresist material or PDMS, and in some cases using a sacrificial layer for ease of separation from a substrate layer.

BACKGROUND OF THE INVENTION

Topical delivery of drugs is a very useful method for achieving systemic or localized pharmacological effects, although there is a main challenge involved in providing sufficient drug penetration across the skin. Skin consists of multiple layers, in which the stratum corneum layer is the outermost layer, then a viable epidermal layer, and finally a dermal tissue layer. The thin layer of stratum corneum represents a major barrier for chemical penetration through the skin. The stratum corneum is responsible for 50%–90% of the skin barrier property, depending upon the drug material's water solubility and molecular weight.

An alternative to the use of hypodermic needles for drug delivery by injection is disclosed in U.S. Pat. No. 3,964,482 (by Gerstel), in which an array of either solid or hollow microneedles is used to penetrate through the stratum corneum and into the epidermal layer. Fluid is dispensed either through the hollow microneedles or through permeable solid projections, or perhaps around non-permeable solid projections that are surrounded by a permeable material or an aperture. A membrane material is used to control the rate of drug release, and the drug transfer mechanism is absorption.

Other types of microneedle structures are disclosed in WO 98/00193 (by Altea Technologies, Inc.), and in WO 97/48440, WO 97/48441, and WO 97/48442 (by Alza Corp.). In addition, WO 96/37256 discloses another type of microblade structure.

The use of microneedles has one great advantage in that intracutaneous drug delivery or drug sampling can be accomplished without pain and without bleeding. As used herein, the term "microneedles" refers to a plurality of elongated structures that are sufficiently long to penetrate through the stratum corneum skin layer and into the epidermal layer. In general, the microneedles are not to be so long as to penetrate into the dermal layer, although there are circumstances where that would be desirable. Since microneedles are relatively difficult to manufacture, it would be an advantage to provide methodologies for constructing microneedles that are made from various types of micromolds that can be manufactured relatively quickly. The use of metallic molds or semiconductor molds is possible, but such structures usually take a relatively long period of time for construction. On the other hand, if the molds are made of a polymer or other type of plastic (or other moldable) material, then such mold structures can be made relatively quickly and with much less expense.

SUMMARY OF THE INVENTION

Accordingly, it is an advantage of the present invention to provide a method for fabricating microneedles using photolithography and soft lithography techniques, which allow for quick manufacturing of both micromolds and usable microneedle structures.

It is another advantage of the present invention to provide a method for fabricating microneedles in which a photoresist material is applied in a single layer, or in multiple layers, and patterned via photolithography, thereby either creating a microneedle structure that can be directly used, or creating micromold structure that can be used with moldable material such as polymers to manufacture the microneedle structures.

It is a further advantage of the present invention to provide a method for fabricating microneedles in which soft lithography is used to create microneedle structures that can be directly used, or to create micromold structures that can be used with moldable material such as polymers to manufacture the microneedle structures, in which a moldable material has its shape formed, at least in part, by another relatively "soft" material—e.g., something other than a metal.

It is still another advantage of the present invention to provide a method for fabricating microneedles in which soft lithography is used to create microneedle structures that can be used to create flexible micromold structures that can be used with moldable material such as polymers to manufacture the microneedle structures, in which the resulting microneedle array is either concave or convex in overall shape.

It is yet a further advantage of the present invention to provide a method for fabricating microneedles in which photolithography and/or soft lithography is used to create micromold structures, and in which a sacrificial layer of material is dissolved or decomposed to separate the micromold structures from a substrate.

It is still a further advantage of the present invention to provide a method for fabricating microneedles in which photolithography and/or soft lithography is used to create microneedle structures, and further coating a surface of the microneedle structures using a vapor deposition process, and/or another coating process such as: electroplating, electrodeposition, electroless plating, sputtering, or plasma deposition.

It is yet another advantage of the present invention to provide a method for fabricating microneedles in which photolithography and/or soft lithography is used to create master structures, and further using a microembossing or molding process to manufacture microneedle structures.

It is still another advantage of the present invention to provide a method for fabricating microneedles in which photolithography and/or soft lithography is used to create microneedle structures, and further creating electrodes on the microneedle structures, either in "bands" of electrically conductive material that each encompass multiple microneedles, or in individual small electrically conductive structures that run inside a single hollow microneedle.

It is a further advantage of the present invention to provide a method for fabricating microneedles in which photolithography and/or soft lithography is used to create microneedle structures, in which the tips of the microneedles are either hardened or made more flexible, or in which the base (or substrate) of the microneedle array is made more flexible, or in which the microneedles break away from the base (substrate) of the array after application to skin, thereby leaving behind hollow microtubes that protrude through the stratum corneum.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a method for fabricating microneedles is provided including steps of: (a) providing a substrate that includes multiple microstructures; (b) coating the substrate with a layer of a first moldable material that takes the negative form of the microstructures, and hardening the first moldable material; (c) separating the hardened first moldable material from the substrate, and creating a micromold from the hardened first moldable material containing the microstructures; and (d) applying a second moldable material onto the micromold, allowing the second moldable material to harden using a soft lithography procedure, then separating the hardened second moldable material from the micromold, thereby creating a microneedle structure from the hardened second moldable material having the three-dimensional negative form of the microstructures of the patterned micromold.

In accordance with another aspect of the present invention, a method for fabricating microneedles is provided including steps of: (a) providing a substrate material; (b) coating the substrate material with at least one layer of a photoresist material, and patterning the photoresist material with multiple microstructures by use of a photolithography procedure; and (c) separating the patterned photoresist material from the substrate material, thereby creating a microneedle structure from the patterned photoresist material containing the microstructures.

In accordance with a further aspect of the present invention, a method for fabricating microneedles is provided including steps of: (a) providing a substrate material; (b) coating the substrate material with at least one layer of a photoresist material, and patterning the photoresist material with multiple microstructures by use of a photolithography procedure; (c) coating the patterned photoresist material with a layer of moldable material that takes the negative form of the microstructures, and allowing the moldable material to harden using a soft lithography procedure, then separating the hardened moldable material from both the patterned photoresist material and the substrate material; and (d) coating at least one surface of the separated hardened moldable material by use of a vapor deposition procedure.

In accordance with yet a further aspect of the present invention, a method for fabricating microneedles is provided including steps of: (a) providing a substrate material; (b) coating the substrate material with at least one layer of a photoresist material, and patterning the photoresist material with multiple microstructures by use of a photolithography procedure; (c) applying a first moldable material onto the patterned photoresist material/substrate and allowing the first moldable material to harden using a soft lithography procedure, then separating the hardened first moldable material from the patterned photoresist material/substrate to create a microstructure; and (d) molding or embossing a second moldable material onto the microstructure, and after hardening of the second moldable material, separating the hardened second moldable material from the microstructure, thereby creating a microneedle structure from the hardened second moldable material having the three-dimensional negative form of the microstructure.

In accordance with still a further aspect of the present invention, a method for fabricating microneedles is provided including steps of: (a) providing a substrate material; (b) coating the substrate material with at least one layer of a photoresist material, and patterning the photoresist material with multiple microstructures by use of a photolithography procedure, such that the patterned photoresist material comprises the microstructures; (c) coating the substrate with a layer of moldable material that takes the negative form of the microstructures, and hardening the moldable material by a soft lithography procedure; (d) separating the hardened moldable material from the substrate, thereby creating a mask; (e) providing a microneedle array structure having multiple individual protrusions extending from a base; and (f) positioning the mask proximal to the microneedle array structure and applying an electrically conductive substance through the mask onto a surface of the microneedle array structure, thereby creating at least one pattern of electrically conductive pathways on the surface.

In accordance with still another aspect of the present invention, a microneedle structure is provided which comprises a longitudinal element having a first end and a second end, in which the longitudinal element has a side wall extending between the first end and the second end; and the side wall also has at least one external channel running between substantially the first end and the second end.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE INVENTION

Figure 1A:
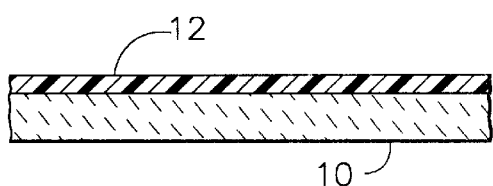
FIGS. 1A–1F are diagrammatic views in cross-section that illustrate some of the process steps for manufacturing polymeric microneedles by replica molding, in which PDMS molds are prepared by employing a photoresist master.

Reference will now be made in detail to the present preferred embodiment of the invention, an example of which is illustrated in the accompanying drawings, wherein like numerals indicate the same elements throughout the views.

Using the principles of the present invention, polymeric microneedles can be fabricated by replica molding in which PDMS molds are prepared using a photoresist master. Alternatively, polymeric microneedles can be made by replica molding in which PDMS molds are made utilizing a silicon wafer that is fabricated by deep reactive ion etching or any other etching technique known by those skilled in the art. In both cases, the PDMS material becomes a negative replica which is used as a mold that can be later filled with a prepolymer material that will itself become an array of microneedles. Both solid and hollow microneedles can be made by the techniques of the present invention.

Although the term "PDMS" is used throughout this patent document in very many places, it will be understood that other materials could instead be used with the present invention in lieu of PDMS, depending upon the microfabrication process of choice. In a replication molding procedure, one could use any moldable material having low surface energy, and the consequent poor adhesion with most substrates. For sacrificial layers, highly reactive polymers or other materials that are soluble in organic or inorganic solvents could replace PDMS. Furthermore, silanization will not generally be necessary if totally inert elastomers are used for replication (e.g., fluorinated polymers). PDMS™ is manufactured by Dow Corning Corporation of Midland, Mich.

In the situation where a photoresist material is used, this material is patterned by use of photolithography techniques, and the patterned structure is used to create the PDMS negative replica. The precise design for the transparency mask used in the photolithography procedures utilizes a microfabrication method that is based on a rapid prototyping technique which uses design software and a high resolution printer; however, masks prepared using the traditional methodologies known by those skilled in the art can also be implemented using this process. The present invention makes good use of photolithography, generally using SU-8 photoresist materials, and a combination of replica molding using soft lithography, electroplating or microembossing processes. Such processes are less expensive and have quicker turnaround time (e.g., less than twenty-four hours) than those previously known in the art for the fabrication of microneedles.

Although the term "SU-8" is used throughout this patent document in very many places as an example of photoresist material, it will be understood that other materials could instead be used in lieu of SU-8, which is a particular brand of photoresist manufactured by MicroChem Corporation of Newton, Mass. SU-8™ has some particularly desirable characteristics, in that as a photoresist it can produce a film thickness greater than or equal to thirty (30) microns. Of course, if the designer wishes to produce a photoresist film having a thickness less than 30 microns, then certainly other photoresist materials could be used. Moreover, photoresist materials other than SU-8 that produce film thicknesses greater than 30 microns may be available, or may become available, and those could perhaps be advantageously used in the present invention.

The present invention not only uses photolithography for patterning certain structures, but also uses "soft lithography" for creating structures in three dimensions using molds made of a polymer material or similar non-metallic material. The soft lithography is a methodology in which all members involved share a common feature in that they use a patterned elastomer as the mask, stamp, or mold. (See, "Soft Lithography," by Younan Xia and George M. Whitesides," Angew. Chem. Int. Ed. 1998.37.550–575.) This elastomeric stamp or mold transfers its pattern to the "moldable material" which can comprise flexible organic molecules or other materials, rather than rigid inorganic materials now commonly used in the fabrication of microelectronic systems. In the present invention, such soft lithography processes are utilized in almost every methodology for creating an array of microneedles.

Professor George Whitesides and colleagues have used soft lithography in numerous microfabrication processes, including: fabrication of carbon microstructures utilizing elastomeric molds (see published patent application, WO 98/34886 A1), etching of articles via microcontact printing (see WO 98/34886 A1), microcontact printing of catalytic colloids (see WO 97/34025), fabrication of small coils and bands by patterning cylindrical objects with patterns of self-assembled monolayers (see WO 97/44692 and WO 97/07429), formation of articles via capillary micromolding (see WO 97/33737), and the utilization of elastomeric masks to fabricate electroluminescent displays (see WO 99/54786).

Silicon masters fabricated using conventional silicon micromachining technologies such as deep reaction ion etching, or structures prepared using LIGA processes, also can be employed for replica molding of microneedles. Such silicon masters will generally require more time in creating the replica molds as compared to the microfabrication methods of the present invention that create mold replicas using photoresist or PDMS (or similar) materials.

The methodologies described below can be used to manufacture solid, partially hollow, or totally hollow microneedles, and such microneedles can be made of electrodepositable metals, thermoplastics, or polymers that cure using heat energy, light energy, or by the addition of an initiator under normal conditions. When photolithography techniques are used, then the light energy is generally used for both patterning and curing the materials, although the curing methodologies can certainly involve other types of energy sources than light.

As noted above, the fabrication techniques described in this document have quicker turnarounds than many others that have been described in the prior art for the fabrication of microneedles. The replica mold can often be made of PDMS material, which is formed into the appropriate shapes by use of a silicon or metallic structure that has been entirely formed to the proper shape, or a silicon wafer structure that has predetermined protrusions that are made of a photoresist material, in which the photoresist was patterned using photolithography techniques. Once the PDMS mold negative replica has been formed, it can be filled with a prepolymer or other type of moldable material, in which the prepolymer or other material becomes the actual array of microneedles. The prepolymer is then cured in a soft lithography process step.

An alternative fabrication technique is to begin with a layer of photoresist material that is separated from a silicon wafer or other substrate material by a "sacrificial layer," made of a material such as PDMS or silicon oxide. One fabrication technique is to place a first layer of photoresist that is cured without using a mask, and then placing a second layer of photoresist that is patterned using photolithography or other patterning techniques. The first photoresist layer later becomes the substrate or base of a microneedle array, while the second layer of photoresist material later becomes the actual protrusions that create the microneedle structures, either solid or hollow. Once the photoresist layers are completely patterned and cured, the sacrificial layer is then dissolved or otherwise decomposed, thereby separating the silicon wafer initial substrate from the microneedle array.

As noted above, the fabrication procedures can be used to make either solid or hollow microneedles. If hollow microtubes are to be created from a silicon wafer having a photoresist top layer, then the top layer of photoresist is patterned as an array of hollow microtubes using photolithography techniques. After that has occurred, the "wafer/patterned photoresist" is silanized and coated with a PDMS material that is cured in a soft lithography process. Once the PDMS has been cured, it is separated from the original silicon wafer/substrate and patterned photoresist combination, thereby producing a negative replica comprising PDMS. The negative replica is then filled with a prepolymer material that is cured with electromagnetic energy or heat energy in a soft lithography process, and once cured the prepolymer is detached from the PDMS mold replica, thereby forming an array of hollow microneedles. At this point, the microneedles may not be completely hollow, as the through-holes only go so far into the photoresist material. Of course, these "microcups" can be opened by laser ablation, or some other type of microfabrication technique.

An alternative methodology for creating hollow microneedles or "microtubes" is to begin with a silicon wafer or other substrate material, place a sacrificial layer on its top, and further place a layer of photoresist above that sacrificial layer. This first layer of photoresist is cured without using a mask, and then it is covered with a second layer of photoresist that is baked to dryness. An array of microneedles or "microtubes" is then formed in the second layer of photoresist by photolithography techniques. Once this has occurred, the sacrificial layer is dissolved or otherwise decomposed, thereby leaving behind an array of microneedles made of the photoresist material. At this point, the microneedles may not be completely hollow, as the through-holes only go so far into the photoresist material. Of course, these "microcups" can be opened by laser ablation, or some other type of microfabrication technique.

Once hollow microtubes or microcups have been formed on a silicon wafer or other substrate, they can be made more detachable in skin by an application of an acid along the base of the outer walls of the microneedles, to thereby etch away a small portion of the material at the base. This will make it more likely that the microneedles can easily detach from the main base or substrate of the microneedle array. This is useful in situations where the microneedles are used to penetrate the stratum corneum of skin, and then have the array base or substrate removed from the skin surface. The microneedles will break away from that substrate/base at that time, thereby leaving hollow microneedles within the stratum corneum. Such microneedles will stay embedded in the stratum corneum until the stratum corneum is renewed, thereby providing a location on the skin where liquids temporarily can be introduced or extracted.

Break-away microneedles can also be made by use of PDMS materials or other coatings that have poor adhesion with photopolymers as the substrate and a photoresist material that makes up the actual microneedles. Such photoresist hollow microneedles would likely break away from the PDMS substrate/base of the microneedle array upon application into the stratum corneum of skin. This would then leave behind multiple such hollow microneedles in the stratum corneum once the array's base/substrate is removed.

The present invention also provides procedures that can fabricate hollow microneedles using deposition techniques. Both metallic hollow microneedles and polymeric hollow microneedles can be constructed in such a manner. The metallic hollow microneedles are made by creating a PDMS negative replica that is then electroplated onto the microneedle structure. This would typically produce "closed" microneedles, which could have their own usefulness, although in many cases the microneedles will be opened to create microtubes with through-holes by use of some type of polishing operation.

Polymeric hollow microneedles can be constructed using deposition techniques by creating a negative PDMS replica and electrodepositing a polymer on "posts" or other microneedle-type structures that are constructed from the PDMS. Once the polymer has been plated on the PDMS, the plated polymer is separated from the PDMS mold, thereby leaving behind multiple microneedle structures that have the form of "closed" microneedles. Such microneedles can be opened to create completely through-hole hollow microneedles by a polishing operation.

The principles of the present invention can also be used to manufacture hollow microneedles using complimentary molds made of PDMS. In this situation, two separate silicon wafers, for example, can be used as starting points in which each are coated with a layer of photoresist material. Using photolithography techniques, each of these wafers has its photoresist layer patterned; in the first case holes are formed in the photoresist layer, and in the second case posts or other similar structures are formed in the photoresist. These patterns will be complimentary, as will be seen below. Both wafers are now silanized and coated with PDMS. The PDMS is cured, and once cured, the PDMS forms a negative replica that can be removed or detached from their respective silicon wafers. The photolithography stage forms both holes and "posts" that are complimentary to one another, and therefore, the two negative replicas made of PDMS are also complimentary. One of these negative replicas is turned upside down, a layer of prepolymer is then placed on top of that "turned-around" PDMS negative replica, and then the second negative replica is placed on top of the prepolymer, thereby sandwiching the prepolymer in place. The prepolymer is now cured and the two PDMS molds are detached, thereby leaving behind a separate polymer structure. If the shape formed "closed" hollow microneedles, then the closed end of these microneedles can be opened by use of some type of finishing or polishing procedure.

Multiple layers of patterns can also be used with the principles of the present invention to create polymeric microneedles, either solid or hollow, as desired. A first layer of photoresist is placed on a silicon wafer or other substrate structure, and holes or other similar patterns are formed in the photoresist by photolithography techniques. A second layer of photoresist is then coated onto this structure, and using a second photolithography procedure, microneedle forms can be made, including hollow tube microneedles. This structure is now silanized, and a PDMS negative replica is formed based upon this pattern. The PDMS now becomes a mold itself, and a polymer material can be placed onto the PDMS negative replica and cured or embossed, thereby forming an array of microneedle structures. If the microneedles form "closed" hollow microneedles, then the closed ends can be removed by polishing or other type of finishing procedure. This would leave behind an array of hollow microneedles having through-holes. Polishing can be avoided by pressing a PDMS flat against the mold filled with prepolymer.

The principles of the present invention can also be used to create microneedles having internal electrodes. Two different initial structures are used to create the electrode-microneedle combinations. On one hand, a polymer microneedle array is constructed according to one of the processes described above, in which the microneedles are hollow with through-holes. The other structure consists of a silicon (or other material) substrate that has a layer of photoresist material applied and patterned using photolithography. This structure is then silanized and coated with PDMS, which is then cured. The cured PDMS layer is then separated from the photoresist-substrate structure, thereby becoming a mask that will be aligned with the hollow microneedles of the first structure. Once the patterned PDMS mask is aligned with the hollow microneedles, metal is vapor deposited on the inside of the microneedles in a pattern that will run through a portion of the length of the hollow microneedles along their inner cylindrical surfaces. Similar masks could also be prepared using electroplating, electroless plating, electrochemical micromachining, silicon or polymer etching.

The electrode-microneedle combination can be constructed so that each hollow microneedle has an electrode that is electrically isolated from each other such hollow microneedle. Alternatively, groups of microneedles can be electrically connected together by use of electrode "bands" in which a first group of multiple microneedles are electrically connected to a "working electrode," a second group of multiple microneedles are connected to a "reference electrode," and finally a third group of multiple microneedles are electrically connected to a "counter electrode."

A reference electrode is not needed in a two-electrode system and, depending upon the electrochemical cell design, microneedle arrays could be used on structures that consist of only one electrode type, such as a working electrode, counter electrode, or reference electrode. These unitary-type electrode structures could be combined in a two-electrode or a three-electrode device. Microneedles are so small in size, that the "electrode bands" might be more useful in certain applications, and the microneedles could be either solid or hollow.

The principles of the present invention can also be used to construct microneedles having a very sharp tip. This could be done by having multiple layers that are patterned one after the other, in which each pattern creates a cylindrical or elliptical opening such that each lower opening is smaller in size than the next adjacent higher opening. This will create a series of photoresist layers, for example, that taper down to a very small opening. When these photoresist structures are finished, they can be separated from a substrate (such as silicon), and this separation could be facilitated by use of a sacrificial layer of material, such as silicon oxide. Once the mold has been separated from the substrate, a polymer or prepolymer material to be placed on top of the mold and forced into the openings that taper down to the smallest opening. Each one of these tapered-down structures, when cured, will become a sharpened tip microneedle. After curing, the array of sharp-tip microneedles is separated from the photoresist mold.

Other types of alternative structures are available when using the principles of the present invention. For example, the base material of the microneedle array can be made from a first structural material, while the microneedles themselves can be made of a second structural material. This allows design freedom to create hydrophobic-hydrophilic combinations and controlled adhesion of the needles to the base. Another alternative structure is to chemically modify the microneedles to change their properties, such as treatment of silicon microneedles with silanizing reagents to derivatize the surfaces. A further alternative structural treatment is the use of a plasma treatment of epoxy or other polymeric microneedles that impart different surface properties (that would affect the hydrophobic or hydrophilic properties). The use of plasma treatment, or chemically modifying the microneedles, can occur at the molecular level, and such processes are commonly referred to as "surface modification" of structures.

Another alternative construction is to incorporate carbon fibers or other composite materials into epoxy microneedles or polymeric microneedles, as well as their substrates, in order to make the substrates and/or microneedles more rigid. Certainly the use of composite materials or carbon fibers could reinforce the microneedles themselves to make them more rigid. Alternatively, such substrates could be made more flexible, including the use of micro channels and grooves in the substrate. It may be likely that the microneedles themselves are to remain rigid in such a structure.

A further alternative construction of microneedles is to make them more flexible, in which the microneedles are rigid enough to break skin, but still have a certain amount of flexibility. This could be used in situations where the microneedles are to penetrate the skin and be held in place for a relatively long period of time. This could be used for continuous monitoring and/or dispensing systems. It would be an advantage to provide such flexible microneedles that would be virtually unbreakable while being used in such circumstances.

Another alternative construction is to place a metal coating over the microneedles as a final outer layer. Several different processes can be used to coat microstructures with metal layers, including electroplating (or electrodeposition), electroless plating, sputtering, vapor deposition, and plasma deposition. It is possible to electroplate some alloys, metal oxides, polymers, and composite materials. Depending on the material that is electroplated, the plating solution can be aqueous or organic.

Electroless plating can be used to deposit metal, oxides, or polymers on virtually any kind of substrates. Sputtering can only be used to deposit thin metal films (from angstroms to nanometers), although sputtering is a fast and inexpensive technique that is convenient to coat non-conductive samples with seed metal layers for a later step of electroplating.

Vapor deposition is preferred over sputtering in the cases where microsmooth metal and oxide films are desired or when common metals do not adhere strongly to the substrates. For vapor deposition, the sample are placed in a vacuum chamber where the metals are evaporated using resistive heating or an electron beam. The metal vapors deposit on the cold areas of the vacuum chamber, including the sample surface. Usually, the specimens are coated with a few angstroms of a metal adhesion layer prior to the deposition of the metal or oxide or interest.

Plasma deposition is a technique that can be employed to deposit very thin films (having a thickness in the order of angstroms) of several kinds of materials on conductive or non-conductive substrates. However, this process typically is slow and expensive. It is normally utilized to prepare films of materials that cannot be handled using the methodologies mentioned above.

One methodology utilizing the principles of the present invention involves fabrication of solid polymeric microneedles using photolithography and replica molding. Two different fabrication schemes are described below, and these are illustrated in FIGS. 1 and 2. "FIG. 1" consists of FIGS. 1A–1F, and illustrates a process that can produce polydimethylsiloxane (PDMS) molds used in the fabrication of solid microneedles that are made of thermally light, or self-curable polymers or by embossing thermoplastics. The first step in the microfabrication method of the present invention is to spin-coat a layer that is about 20–200 microns in thickness of a photoresist compound (e.g., SU-8) on a silicon wafer, and baking to dryness at 90° C. The silicon wafer is at reference numeral 10, and the photoresist is at reference numeral 12 on FIG. 1A.

Figure 1B:
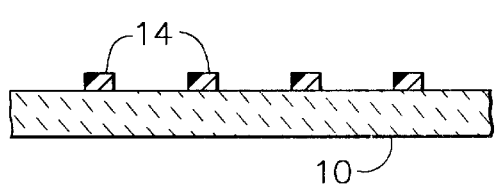
Figure 1C:
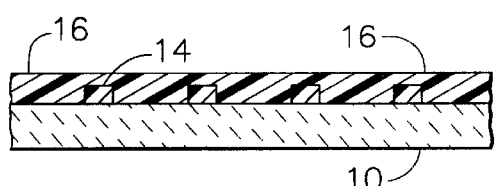

The photoresist film is then patterned with posts 14 having a diameter in the range of 10–100 microns, using photolithography, as illustrated in FIG. 1B. The wafer is then silanized with an alkyl chlorosiloxane compound, then covered with PDMS and cured in an oven at about 60–70° C. for about two hours. This soft lithography step is illustrated in FIG. 1C, where the layer of PDMS is at reference numeral 16.

Figure 1D:

The PDMS negative replica is detached manually from the silicon/SU-8 master, as illustrated by the negative replica 16 of FIG. 1D. Naturally, this detachment operation can be automated.

Figure 1E:
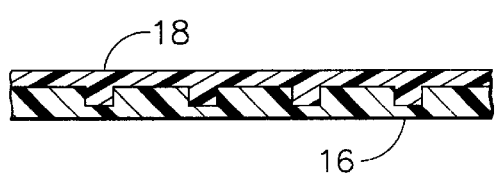
Figure 1F:
Figure 2E:
Figure 3A:
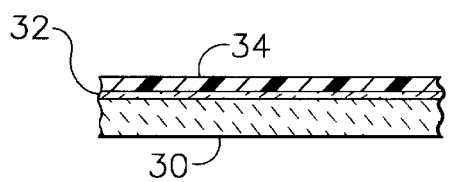
FIGS. 3A–3E are diagrammatic views in cross-section showing the steps employed to construct microneedle arrays made of a photoresist material, in which photolithography is used on a substrate that is coated with silicon oxide.

The PDMS structure is then filled under a vacuum with a photocurable polymer or a prepolymer material, such as epoxy known as UVO-110 under a vacuum. This structure is irradiated with ultraviolet light for two hours using a mercury lamp, or other ultraviolet light source to cure the prepolymer 18, in a soft lithography process step. This is illustrated in FIG. 1E, in which the prepolymer is at reference numeral 18. Finally, the microneedle structure is separated from the mold, leaving a microneedle array 18 made of polymer as seen in FIG. 1F.

Figure 2A:
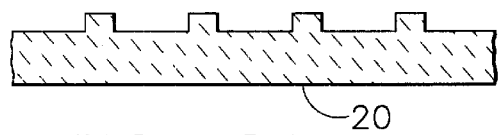
FIGS. 2A–2E are diagrammatic views in cross-section that illustrate some of the process steps for manufacturing polymeric microneedles by replica molding, in which PDMS molds are made utilizing a silicon specimen that was fabricated by deep reactive ion etching (DRIE).

As an alternative methodology, silicon microstructure array masters prepared using deep reactive ion etching (DRIE), or metallic microstructure array masters (prepared using, e.g., LIGA techniques) could be employed instead of the SU-8 photoresist masters to manufacture polymeric microneedles as shown in FIG. 1. This alternative methodology is illustrated in "FIG. 2," which consists of FIGS. 2A–2E. In FIG. 2A, the silicon microstructure array master is illustrated at the reference numeral 20. As noted above, instead of a silicon structure, the microstructure could be made of a metallic substance.

Figure 2B:
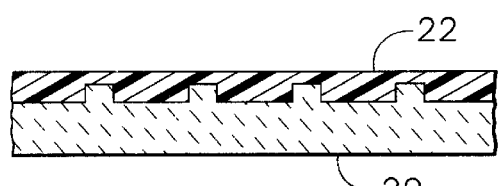

The silicon structure 20 is then silanized and covered with PDMS at 22, as seen in FIG. 2B. After being covered with the PDMS material, the structure is cured in an oven at about 60–70° C. for about two hours.

Figure 2C:
Figure 2D:

The PDMS negative replica is detached from the silicon or metallic master 20, leaving the negative replica structure 22, as viewed in FIG. 2C. The PDMS structure 22 is then filled with a photocurable polymer at 24, as seen in FIG. 2D. This photocurable polymer is then exposed to a light source, such as an ultraviolet light source from a mercury lamp. This cures the polymer, and the microneedle apparatus is then separated, leaving the microneedle array 24, as viewed in FIG. 2E. An example of an ultraviolet-curable polymer is a compound known as Uv-114, manufactured by Epoxy Technologies Inc.

The process described in FIG. 1 can be modified to generate freestanding photoresist microneedle devices, examples of which are illustrated in FIGS. 3 and 4 with respect to their construction techniques. "FIG. 3" consists of FIGS. 3A–3E. An oxidized silicon wafer at 30 includes a top layer of PDMS at 32, which is coated with a layer of photoresist material at 34, as viewed in FIG. 3A. This structure is baked to dryness and cured with ultraviolet light to obtain a solid film of the cured photoresist material at 36 (see FIG. 3B). An example of this photoresist material is SU-8. The structure of FIG. 3B is coated again with photoresist, in this case a layer 38 in the range of 20–200 microns thick. This structure is baked to dryness at approximately 90° C., providing the structure of FIG. 3C in which the second layer of photoresist is illustrated at the reference numeral 38.

Microneedles are formed in the second layer of photoresist 38 by a photolithography technique using a transparency mask patterned with dots having a diameter in the range of 20–100 microns. This provides the structure of FIG. 3D, in which solid microneedles at 40 are formed in an array-type structure.

Figure 3B:
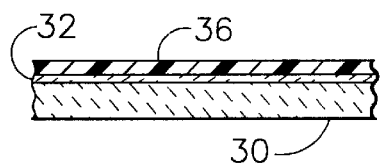
Figure 3C:
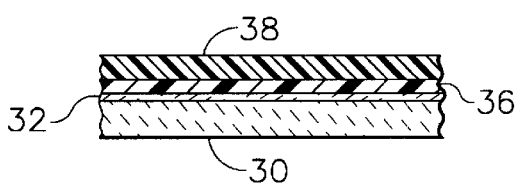
Figure 3D:
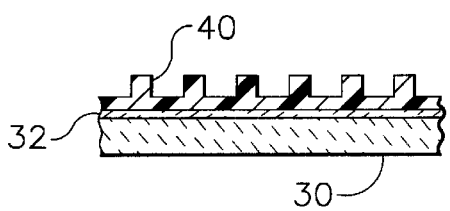
Figure 3E:

The microneedle structure is separated from the wafer by dissolving a "sacrificial layer" with an appropriate reagent, in which the PDMS layer 32 is decomposed with tetrabutylammonium fluoride (TBAF) and tetrahydrofuran, leaving behind the microneedle array structure 40 of FIG. 3E.

Figure 4A:
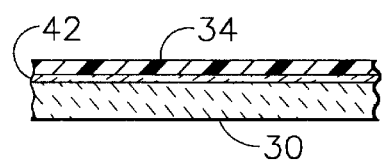
FIGS. 4A–4E are diagrammatic views in cross-section showing the steps employed to construct microneedle arrays made of a photoresist material, in which photolithography is used on a substrate that is coated with PDMS.
Figure 4B:
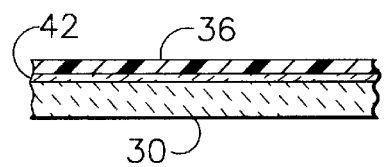
Figure 4C:
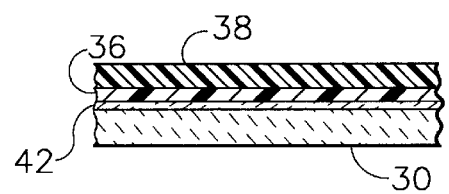

An alternative methodology for generating a freestanding photoresist material microneedle array is described in connection with "FIG. 4," which consists of FIGS. 4A–4E. In FIG. 4A, an oxidized silicon wafer 30 which includes a layer of silicon oxide at 42, is coated with a layer of photoresist material 34 and baked to dryness. The photoresist layer 34 is exposed without using a mask and cured, which is illustrated at the reference numeral 36 in FIG. 4B. The wafer structure is then coated with a second layer of photoresist material at 38 and baked to dryness at about 90° C., which is illustrated in FIG. 4C.

Figure 4D:
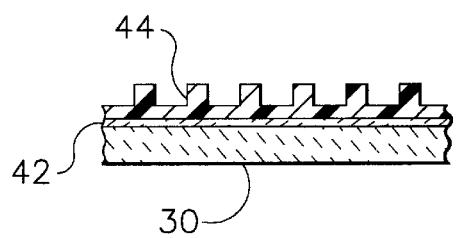
Figure 4E:
Figure 5A:
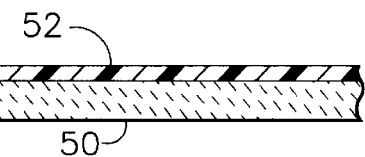
FIGS. 5A–5F are diagrammatic views in cross-section showing the various steps employed to fabricate hollow microneedles using deposition techniques, in which metallic hollow microneedles are made by electroplating on a PDMS structure.
Figure 5B:
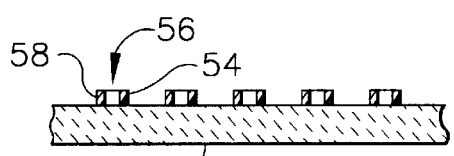

Microneedle-like structures are formed in the second photoresist layer by a photolithography procedure using a transparency mask that is patterned with dots having a general diameter in the range of 20–100 microns. This is the structure illustrated in FIG. 4D, in which the top layer 44 is the second photoresist layer that has microneedle structures protruding upwards in the figure. The wafer structure is then immersed in hydrofluoric acid (e.g., 10% solution) to detach the polymeric structure from the silicon substrate. This provides the separate microneedle (polymeric) structure at 44, as illustrated in FIG. 4E. The silicon oxide layer 42 acts as a sacrificial layer by dissolving or otherwise decomposing in the hydrofluoric acid.

The array of solid microneedles in FIGS. 3E at 40 and 4E at 44 can be converted into "hollow" microneedles by various techniques. One well known technique is laser ablation, which would essentially burn holes through the centerline (or approximately near the centerline) of each of the cylindrical microneedle structures.

One aspect of the present invention is to create microneedle arrays that include individual microneedles that exhibit a "high aspect ratio." The overall length of a microneedle divided by its overall width is equal to the aspect ratio. If a microneedle is 200 microns in length, and its width (or diameter if it is circular) is 50 microns, then its aspect ratio is 4.0. It is desirable to use a relatively high aspect ratio of at least 3:1, although creating such structures can be difficult.

The microneedles are so tiny in actual size (especially in the smaller widths or diameters) that it is not an easy task to make them sufficiently strong to penetrate the stratum corneum of skin without breaking. So there is a trade-off; one cannot merely make the microneedles "thicker" (or wider), because there needs to be some open area between each of the microneedles in the array to allow the tips of the microneedles to actually penetrate the outer skin layer. This aspect of the use of microneedles is described in detail in a patent application that is assigned to The Procter & Gamble Company, under Ser. No. 09/328,947 which was filed on Jun. 9, 1999, and titled "Intracutaneous Microneedle Array Apparatus." This patent application is incorporated herein by reference in its entirety.

At the same time, one cannot merely make the microneedles shorter to decrease the chance of their being broken upon insertion into skin. The individual microneedles should be longer than the thickness of the stratum corneum, or they will not sufficiently increase the permeability of the skin to the fluid of interest. These constraints call for a structure that is relatively high in aspect ratio in most instances (such as 3:1, noted above).

Two different methodologies for fabricating hollow microneedles are illustrated in FIGS. 5 and 6, and are described immediately below. "FIG. 5" (which comprises FIGS. 5A–5F) starts with a silicon wafer at 50 with a top layer of photoresist at 52 (see FIG. 5A). One preferred methodology for creating this structure is to use a spin-coating procedure to apply a layer of photoresist material that is in the range of 20–200 microns thick on the silicon wafer 50. This structure is baked to dryness at approximately 90° C., and then the photoresist 52 is patterned with hollow cylinders by use of a photolithography procedure, which results in the structure of FIG. 5B. In FIG. 5B, the photoresist material has been formed into multiple hollow tubes at 54, in which each of these hollow tubes comprises a hollow cylinder having a wall 58 and an open hollow space at 56 within these walls 58.

The structure is then silanized with an alkyl chlorosiloxane compound, then covered with PDMS under a vacuum, and cured in an oven in the range of 60–70° C. for approximately two hours in a soft lithography process step. This provides the structure seen in FIG. 5C, in which the PDMS layer is designated by the reference numeral 60.

Figure 5D:
Figure 6D:
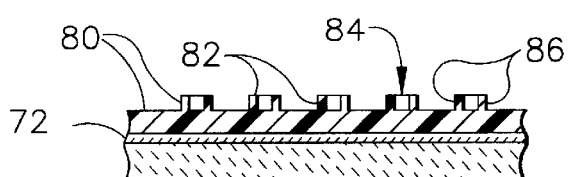

The PDMS mold is separated from the photoresist master, thereby providing the structure 60 by itself, as seen in FIG. 5D. This structure 60 will be used to obtain plastic "microcups."

Figure 5E:
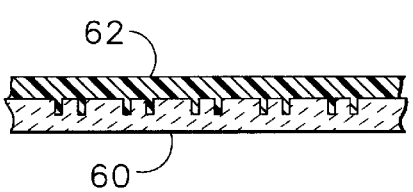
Figure 6E:
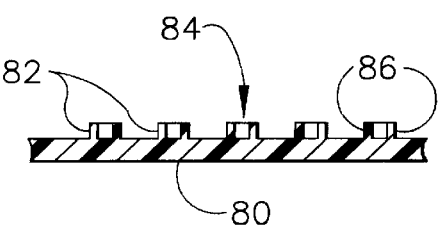
Figure 5F:
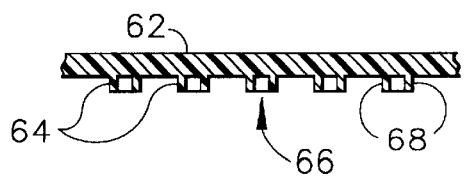

In FIG. 5E, the PDMS mold 60 has been inverted with respect to FIG. 5D. This PDMS mold 60 is now filled with a prepolymer material 62, and this prepolymer is cured with some type of heat energy or with electromagnetic radiation, such as ultraviolet light in another soft lithography process step. Once cured, the prepolymer material 62 is detached from the mold 60, thereby leaving behind the structure 62 as seen in FIG. 5F. As can be seen in FIG. 5F, polymeric microneedles are formed as part of the structure 62, in which each of these microneedles has the form of a "microcup" 64. These microcups include an outer cylindrical wall 68 and a center open volume 66. Of course, these microcups could be made into "microtubes" or other type of hollow microneedle by use of laser ablation, or by some other technique, if desired.

In the procedure illustrated in "FIG. 5," the hollow microneedles or microcups were formed using PDMS molds. As an alternative methodology for fabrication, photolithography of a photoresist mounted on a substrate covered with a sacrificial film could be utilized, as will now be discussed in reference to "FIG. 6," which consists of FIGS. 6A–6E.

Starting with a silicon wafer 70, having a layer of either PDMS or silicon dioxide material at 72, a layer of photoresist material 74 is applied, preferably by spin-coating. This is the structure illustrated in FIG. 6A. This structure is then baked to dryness at approximately 90° C. If PDMS is used for layer 72, it could have a thickness of approximately 100 microns, or if silicon oxide is used, its thickness could be much smaller, on the order of 500 nm.

Figure 6A:
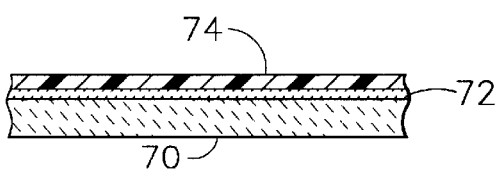
FIGS. 6A–6E are diagrammatic views in cross-section showing the various steps employed to fabricate hollow microneedles using deposition techniques, in which polymeric hollow microneedles are constructed by electrodeposition on PDMS posts.
Figure 6B:
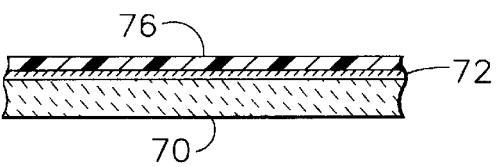
Figure 5C:
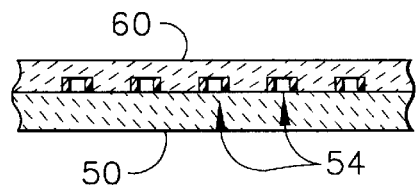

After being baked, the structure has the appearance as illustrated in FIG. 6B, in which the silicon wafer 70 and intermediate layer 72 is topped by a cured or "baked" layer of photoresist at 76.

Figure 6C:
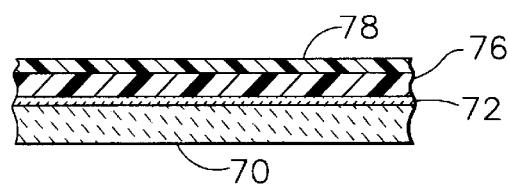

This structure is then coated again with a further layer of photoresist at 78, as viewed in FIG. 6C. This structure is then baked, and patterned with a transparency mask using photolithography techniques. This provides the structure as viewed in FIG. 6D, in which multiple hollow structures 82 are formed as part of an overall photoresist layer 80. These hollow structures 82 are also in the form of "microcups," similar to those disclosed in reference to FIG. 5F.

The microcups 82 each have a cylindrical wall 86, as well as a hollow volumetric space at 84 within the cylindrical walls 86. This microneedle or microcup array structure 80 can be readily detached from the substrate, thereby leaving behind the array structure as viewed in FIG. 6E. This could involve dissolving the sacrificial layer 72, which if the sacrificial layer consisted of PDMS would involve TBAF (tetrabutylammonium fluoride) in THF (tetrahydrofuran); if the sacrificial layer consisted of silicon dioxide, then the dissolving fluid would be 10% hydrofluoric acid.

Figure 7X:
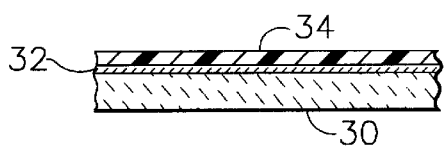
FIGS. 7A–7B, 7X–7Z are diagrammatic views in cross-section showing some of the structural steps used in fabricating arrays of detachable microtubes, in which photolithography is used on a wafer coated with PDMS.
Figure 7Y:
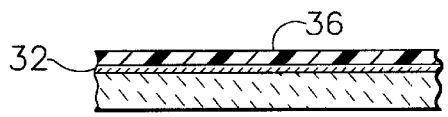
Figure 7Z:
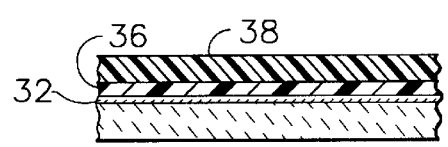

Wafers that have been coated with sacrificial layers can also be used to fabricate hollow microtubes that can be easily detached from the base structure or substrate of the microneedle array, upon the application of small forces. Such detachable hollow microneedles or microtubes can be used to open momentary cavities across the stratum corneum of the skin. These cavities are not permanent, due to the natural shedding process of the stratum corneum. One methodology for constructing such detachable hollow microtubes is illustrated in "FIG. 7." "FIG. 7" consists of FIGS. 7A–7B and 7X–7Z, but it will be understood that the first three steps of this procedure in FIGS. 7X–7Z involve the structures illustrated in FIGS. 3A, 3B, and 3C.

Figure 7A:
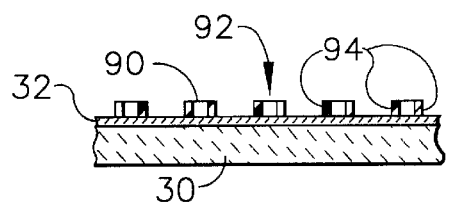

The structure illustrated in FIG. 3C involves a silicon wafer 30, a layer 38 of PDMS material that is baked to dryness. In FIG. 3D, solid microneedles were formed using a photolithography process. In FIG. 7A, instead of solid microneedles, hollow microtubes will be formed, and these structures are indicated at the reference numeral 90.

Figure 7B:
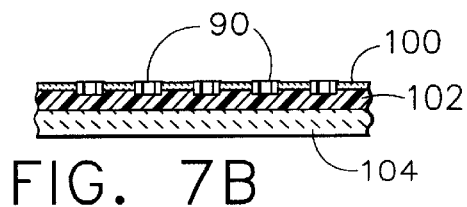

After the silicon wafer has been covered with PDMS and baked to dryness, photolithography is used to make the hollow tubes 90. Each of these hollow microtubes consist of a cylindrical wall portion 94, which encompasses an open volume 92. The microneedles fabricated on the PDMS film (i.e., layer 32) do not need any type of treatment prior to skin penetration, because the adhesion between PDMS and most polymers is relatively weak. Therefore, the microneedles will fairly easily detach upon penetration into the stratum corneum. This is illustrated on FIG. 7B, in which the microtubes 90 are shown in place in the stratum corneum layer 100. The epidermis layer 102 and the dermis layer 104 are also illustrated in FIG. 7B, which of course lie beneath the stratum corneum layer 100.

Figure 8X:
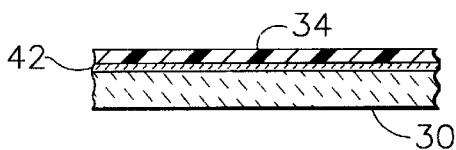
FIGS. 8A–8D, 8X–8Z are diagrammatic views in cross-section showing some of the structural steps used in fabricating arrays of detachable microtubes, in which photolithography on an oxidized silicon wafer.
Figure 8Y:
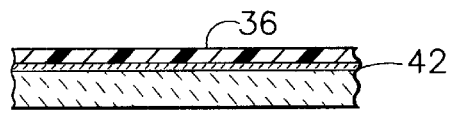
Figure 8Z:
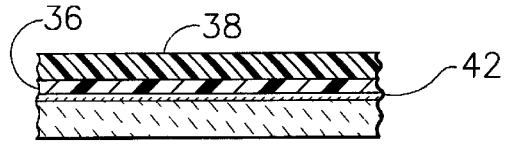

An alternative fabrication methodology would be to use a silicon wafer that has a silicon oxide layer 42, such as that provided by the structure illustrated in FIG. 4C. This alternative fabrication methodology is illustrated in "FIG. 8," which consists of FIGS. 8A–8D and 8X–8Z. It will be understood that the first three process steps in FIGS. 8X–8Z involve structures having the appearance of FIGS. 4A, 4B, and 4C.

The structure of FIG. 4C included a silicon wafer 30, a layer of silicon oxide 42, an upper layer of cured photoresist 36, and a second layer of photoresist at 38 that was baked to dryness. In FIG. 4D, the photolithography process was used to form solid microneedles. However, in FIG. 8A, the transparency mask is used to create hollow microneedles or "microtubes" by the same type of photolithography process.

Figure 8A:
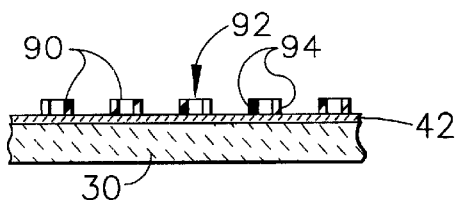
Figure 8D:
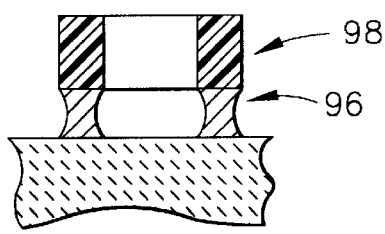

In FIG. 8A, the microtubes 90 are very similar in appearance to those illustrated in FIG. 7A. Each of the microtubes has a cylindrical outer wall 94 that encompasses a hollow volumetric space 92.

Figure 8B:
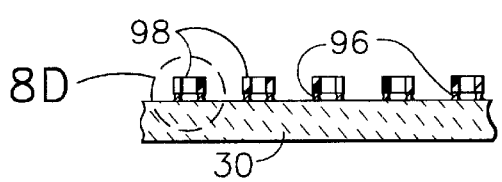

In FIG. 8B, an additional procedure of treating the "sacrificial layer" 42 with hydrogen fluoride (at 10%) for approximately two (2) to five (5) minutes will weaken the needle/substrate interface, as seen at the portion designated by the reference numeral 96. In other words, the hydrogen fluoride treatment will tend to etch away a certain portion of the silicon oxide layer, and leave behind "break away" portions of the cylindrical walls that will facilitate the detachment of the hollow microtubes upon skin penetration. A magnified view of the resulting microtube 98 having the "weakened" (or "break-away") area 96 is provided on FIG. 8D.

One structure that has been successfully tested involves a silicon oxide layer that is approximately 500 nm in thickness, and covered with a photoresist material (e.g., SU-8) of about 20–200 microns that have been baked to dryness at 90° C. This will produce hollow microtubes or microneedles that have a length in the range of about 20–200 microns.

Figure 8C:
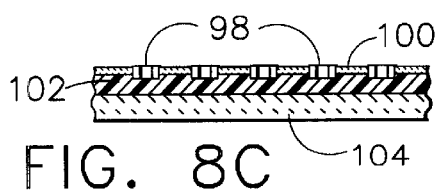

FIG. 8C shows the final result, in which the "break-away" hollow microneedles or microtubes at 98 are embedded in the stratum corneum 100.

Metallic hollow microneedles can also be constructed using photolithography techniques. FIGS. 9 and 10 illustrate some of the steps for two different methodologies of fabricating metallic hollow microneedles. "FIG. 9" consists of FIGS. 9A–9G while "FIG. 10" consists of FIGS. 10A–10G.

Figure 9A:
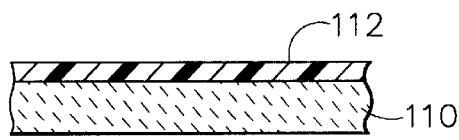
FIGS. 9A–9G are diagrammatic views in cross-section illustrating some of the structural steps employed to fabricate hollow microneedles using deposition techniques, in which metallic hollow microneedles are made by electroplating on a PDMS structure.
Figure 9B:
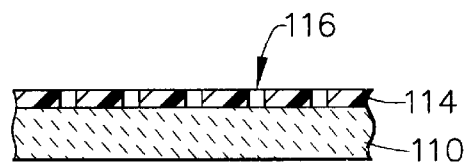

FIG. 9A illustrates a silicon wafer 110 that has had a photoresist layer spin-coated at 112. An example of photoresist material is SU-8, and the thickness of this material could be in the range of 20–200 microns. The photoresist is then patterned with cylindrical holes 116 using a photolithography process, thereby providing the structure in FIG. 9B in which the silicon wafer 110 is now topped by a photoresist layer 114 that has a plurality of such cylindrical holes 116. These holes could have a diameter in the range of 20–100 microns, or virtually any other size, as desired for a particular application.

Figure 9C:
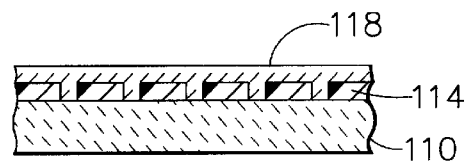

This structure is now silanized and then covered with PDMS material that is cured for about two hours at approximately 60–70° C. in a soft lithography process step. The resulting structure is illustrated in FIG. 9C, in which the silicon wafer 110 and photoresist layer 114 are topped by the cured PDMS 118.

Figure 9D:
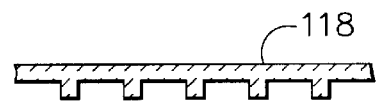

The PDMS negative replica 118 is now removed or detached from the photoresist master, leaving behind the unitary structure 118 that is illustrated in FIG. 9D.

Figure 9E:
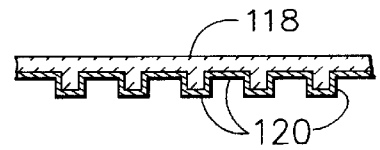

The PDMS mold negative replica 118 is now coated with a metallic substance using sputtering or vapor deposition. This is illustrated in FIG. 9E, in which the PDMS material 118 is coated or plated with a metal layer at 120. One example of this metal coating could be a layer of gold that is approximately 50 angstroms in thickness.

Figure 9F:
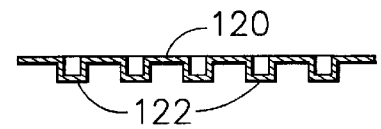

Another example is to use a layer of nickel, copper, gold, platinum, or silver having a thickness in the range of 10–30 microns, by use of an electroplating procedure on the previously coated gold/PDMS structure. This will form an array of metallic needles that can be isolated by dissolving the PDMS layer in a 1 M solution of TBAF in THF, thereby leaving the unitary structure 120 that is illustrated in FIG. 9F.

The structure 120 is the separate metal layer that has been detached from the PDMS mold. This structure 120 includes an array of protrusions at 122, each of which will become the basis for a hollow microneedle or microtube. At this point in the process, the microneedles 122 are essentially "closed"

and have the form of "microcups" in essence, when viewed from above. Of course, when viewed from below, these closed microneedles 122 essentially act as liquid tight microneedles that have the appearance of solid microneedles.

Figure 9G:
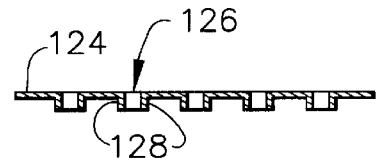

These tubular microneedles 122 are now "opened" by polishing the closed ends by one of several possible techniques, thereby leaving behind an array of hollow microneedles in a unitary array structure 124 that is illustrated in FIG. 9G. Each of the hollow microneedles or "microtubes" 122 includes a cylindrical wall 128 that surrounds a hollow volumetric space 126 that, in this illustrated embodiment, supplies a tubular passageway or through-hole from one surface of the unitary structure 124 to the opposite side of that same structure. The polishing technique described above could be as simple as using sandpaper on the surface where the closed end 122 existed in FIG. 9F, or it could be some type of milling or grinding operation, or finally some non-mechanical technique could be used, such as a laser beam to burn away or vaporize the closed end by laser ablation.

The microneedle arrays could be separated by hand from the PDMS molds and the metallic structures could be synthesized using electroless plating techniques. The molds could be reused if the structures are disconnected by hand. Moreover, the polishing step could be avoided if the tips of the PDMS/gold posts (at 122) were earlier stamped with a non-conductive material such as thiol monolayer or a polymer, or were peeled off using adhesive tape.

An alternative technique for creating metallic microneedles is illustrated in FIG. 10. Starting at FIG. 10A, a silicon wafer 110 that has had a photoresist layer spin-coated at 112 is illustrated (similar to FIG. 9A). An example of photoresist material is SU-8, and the thickness of this material could be in the range of 20–200 microns. The photoresist is then patterned with cylindrical holes 116 using a photolithography process, thereby providing the structure in FIG. 10B in which the silicon wafer 110 is now topped by a photoresist layer 114 that has a plurality of such cylindrical holes 116. These holes could have a diameter in the range of 20–100 microns, or virtually any other size, as desired for a particular application.

Figure 10A:
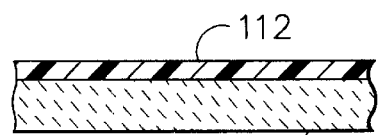
FIGS. 10A–10G are diagrammatic views in cross-section illustrating some of the structural steps employed to fabricate hollow microneedles using deposition techniques, in which polymeric hollow microneedles are constructed by electrodeposition on PDMS posts.
Figure 10B:
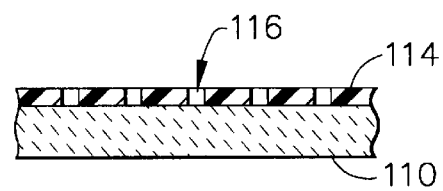
Figure 10C:
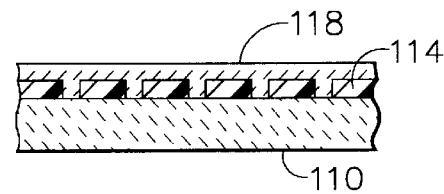

This structure is now silanized and then covered with PDMS material that is cured for about two hours at approximately 60–70° C. in a soft lithography process step. The resulting structure is illustrated in FIG. 10C, in which the silicon wafer 110 and photoresist layer 114 are topped by the cured PDMS 118.

Figure 10D:
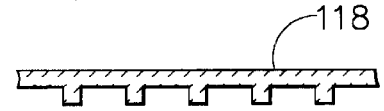
Figure 10E:
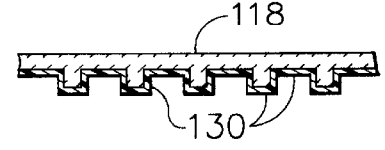

The PDMS negative replica 118 is now removed or detached from the photoresist master, leaving behind the unitary structure 118 that is illustrated in FIG. 10D. The PDMS negative replica 118 of FIG. 10D is now used in a vapor deposition procedure, and then a procedure where polymer is electroplated. The vapor deposition could involve chromium or gold, for example. This would lead to the structure 118 of FIG. 10E, in which the plated polymer layer is at 130.

This particular procedure could also be modified to construct tapered microneedles by overexposing the photoresist master and then fabricate plastic hollow microneedles by electrodepositing the polymers, such as the layer 130 of plated polymer material. Such polymer materials that can be electroplated include POWECRON® acrylic epoxies (manufactured by PPG Industrial Coatings of Pittsburgh, Pa.), and EAGLE 2100® (manufactured by The Shipley Company of Marlboro, Mass.

Figure 10F:
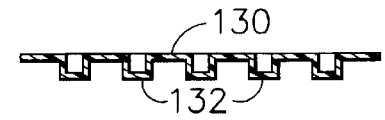
Figure 10G:
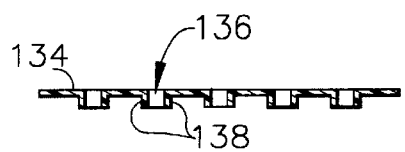

The polymer microneedles are separated from the PDMS mold, thereby leaving behind the unitary structure 130 of FIG. 10F. At this point, the projections that will eventually become tubular microneedles are "closed," as viewed at 132 on FIG. 10F. Therefore, a procedure is performed to "open" the microneedles, by use of some type of polishing technique, similar to that described above in reference to FIG. 9G. This provides the structure 134 illustrated in FIG. 10G. The microneedle array structure 134 includes hollow microneedles or "microtubes," each of which consists of a cylindrical wall 138 that encompasses an open volumetric space 136 that extends from one surface to the other of the microneedle array 134.

"FIG. 11" illustrates a fabrication technique by which microneedles are constructed by curing polymers that are sandwiched between complimentary PDMS structures. "FIG. 11" consists of FIGS. 11A–11K, and beginning at FIG. 11A a silicon wafer 140 is spin-coated with a photoresist material 142, such as SU-8. A second wafer 150 is also spin-coated with a photoresist compound 152, as illustrated in FIG. 11E. The photoresist layer 142 thickness is approximately 175 microns for the wafer 140 of FIG. 11A, while the thickness of the photoresist layer 152 is approximately 200 microns on FIG. 11E.

Figure 11A:
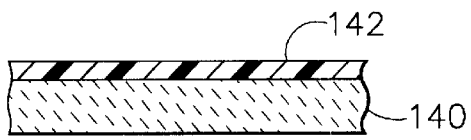
FIGS. 11A–11K are diagrammatic views in cross-section showing the structural steps utilized to manufacture hollow microneedles using complimentary PDMS molds.
Figure 11B:
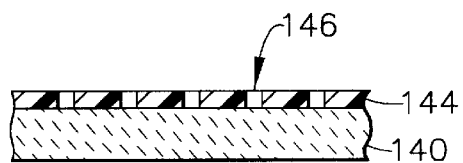
Figure 11C:
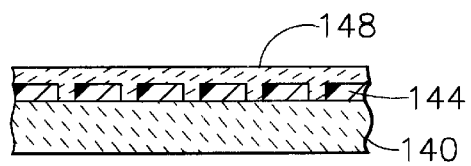

These structures are now patterned using a photolithography process, and an array of holes are formed in the photoresist layer 142, which is illustrated on FIG. 11B by the holes 146, which are bounded by the remaining portions of the photoresist at 144. The separation of these holes is approximately 300 microns, and these cylindrical holes have a height of about 175 microns, and a diameter of about 50 microns.

An array of posts 154 are formed from the photoresist 152 by use of patterning and photolithography techniques, and these posts have a separation of approximately 300 microns with a height of approximately 200 microns and a diameter somewhat less than 50 microns. See FIG. 11F. After the post 154 and holes 146 are formed on their respective structures, both wafers are silanized, covered with PDMS or an equivalent material, and cured at approximately 60° C. for about two hours using soft lithography. This provides the structures illustrated in FIGS. 11C and 11G, in which the PDMS layer 148 protrudes into the "hole" spaces 146 that are between the photoresist structures 144, and the PDMS layer 156 on FIG. 11G, which surrounds the post 154.

Figure 11D:
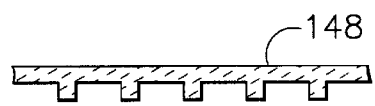
Figure 11E:
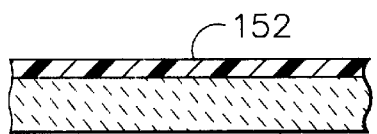
Figure 11F:
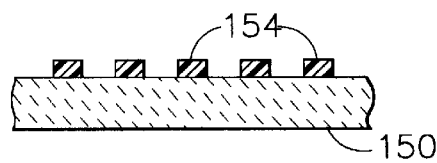
Figure 11G:
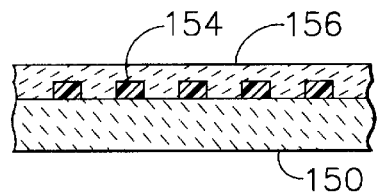
Figure 11H:
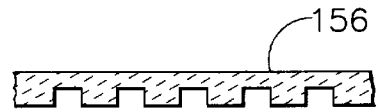
Figure 11I:
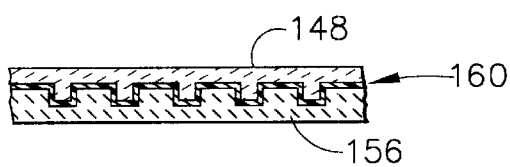
Figure 11J:
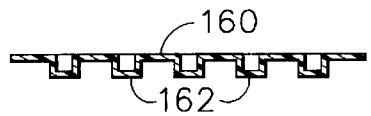
Figure 11K:
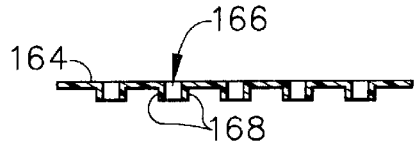

The specimens are now cooled to room temperature, and the PDMS replicas are detached from the wafers, thereby providing the structures 148 and 156, as illustrated in FIGS. 11D and 11H, respectively. One of these replica structures (preferably the structure 156 having the "holes") is now coated with a relatively thin layer of a prepolymer material, such as polyurethane (PU), epoxy, polymethyl methacrylate (PMMA), bone suturing materials, dental polymers, or other similar prepolymer compound. The two structures 148 and 156 are now aligned, in which the posts now resident in the structure 148 are aligned with the "holes" resident in the structure 156. The result is illustrated in FIG. 11I, in which the replica structure having "posts" 148 is fitted atop the replica structure having the "holes" at 156, and in which the above prepolymer material 160 is placed between these two replica structures 148 and 156. Once they are aligned, they are pressed, or held together, and cured as appropriate, using heat energy or perhaps electromagnetic energy, such as ultraviolet light or visible light.

The two PDMS mold replicas 148 and 156 are now separated and the now cured polymer material 160 is separated from both of these mold replicas. This provides the structure illustrated in FIG. 11J, in which the cured polymer array 160 consists of multiple posts or protrusions at 162. These posts/protrusions 162 are not solid, but are hollow, and have a form somewhat similar to a "microcup" as described above. As viewed from above in FIG. 11J, these protrusions would have the appearance of microcups, although when viewed from below, they would have the appearance of solid posts or microneedles.

The purpose of this structure is not necessarily to create solid microneedles or microcups, and therefore, the closed ends at 162 of these protrusions are opened by some type of polishing procedure, thereby forming hollow microneedles or microtubes. These microneedles/microtubes have cylindrical walls at 168 (see FIG. 11K), and the walls 168 surround an empty volumetric space, as illustrated at 166. The polishing procedure could be simply the use of sandpaper, or a more sophisticated or automated procedure using a milling machine or a grinder, for example.

Convex or Concave Microneedle Arrays

Figure 16A:
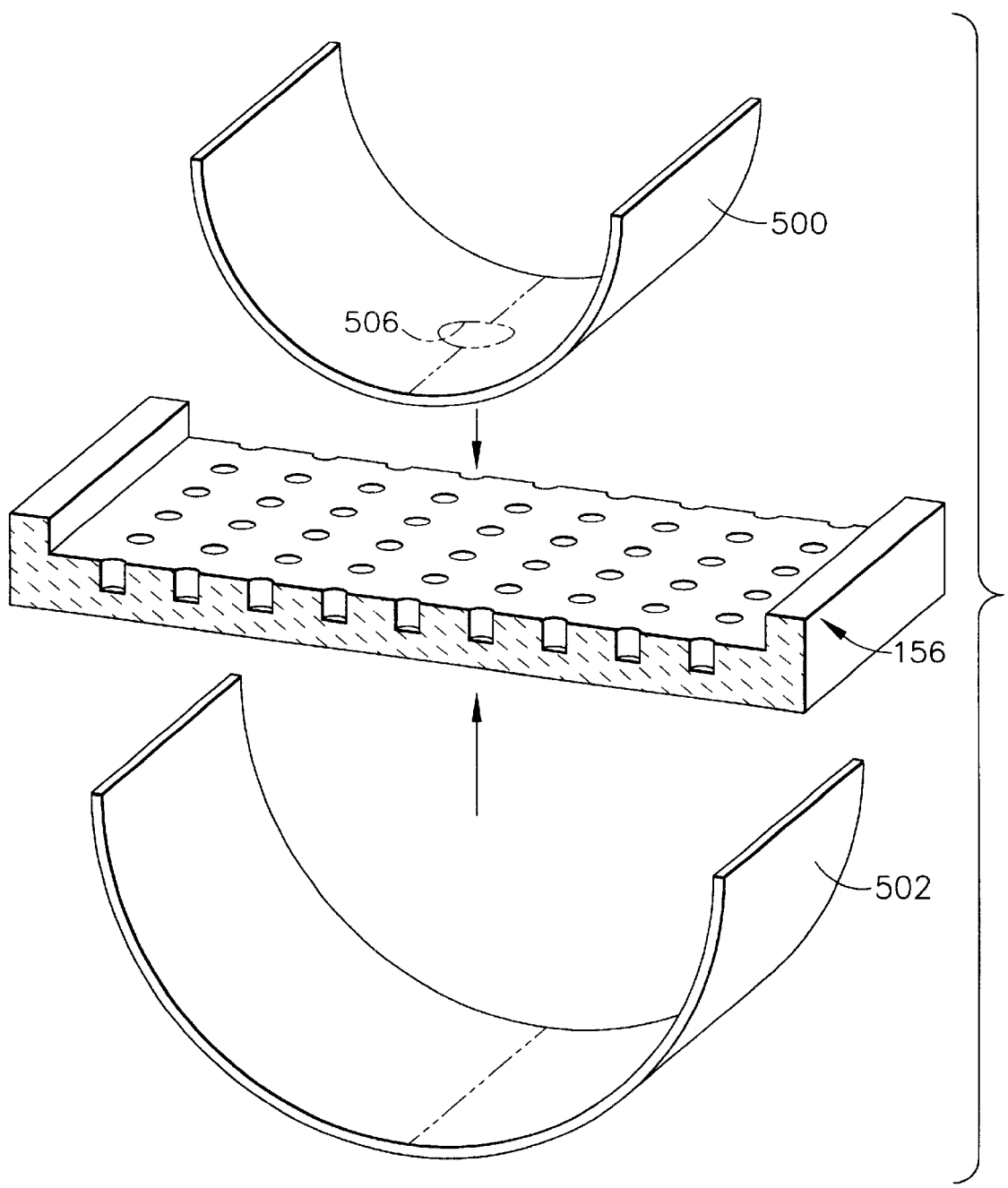
FIGS. 16A–16E are perspective views showing the structural steps utilized to manufacture convex or concave microneedles using flexible molds.

If desired, the mold material 156 of FIG. 11G can be made of a material that has flexibility characteristics. Such a flexible mold can then be used to form microneedle arrays that are convex or concave in overall shape (i.e., the shape of their substrate). Referring now to "FIG. 16" (which comprises FIGS. 16A–16E), the original rectangular shape of the mold 156 is illustrated in FIG. 16A, along with a top mold plate 500 that is convex and a bottom mold plate 502 that is concave.

Figure 16B:
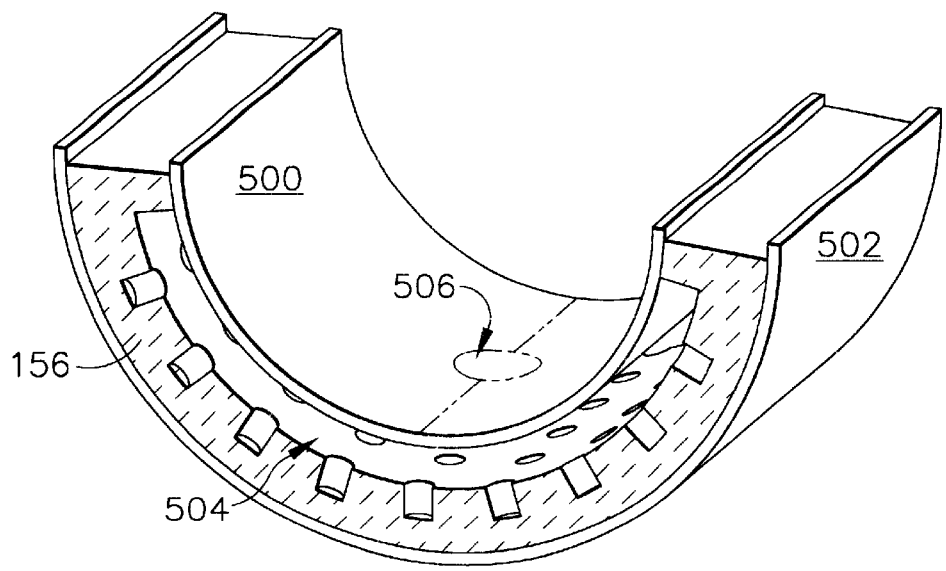
Figure 16C:
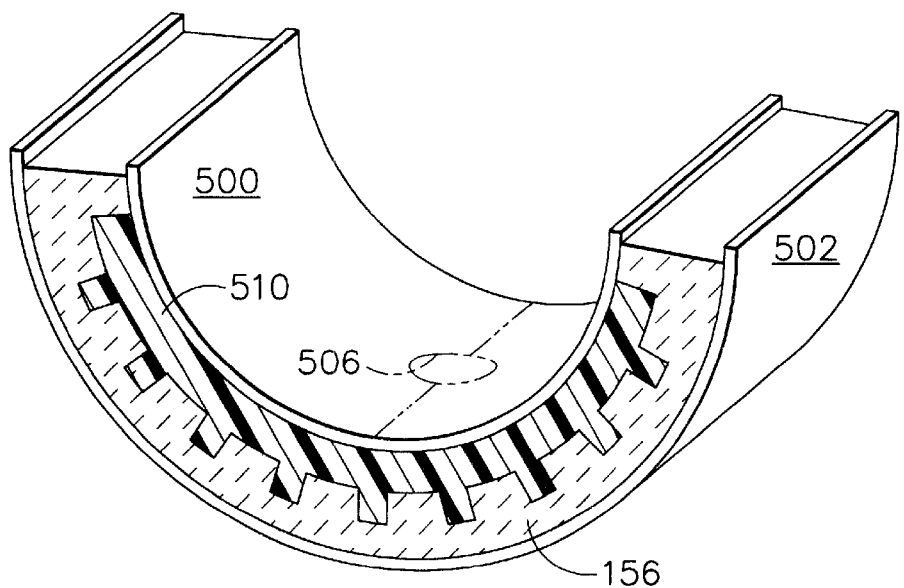
Figure 16D:
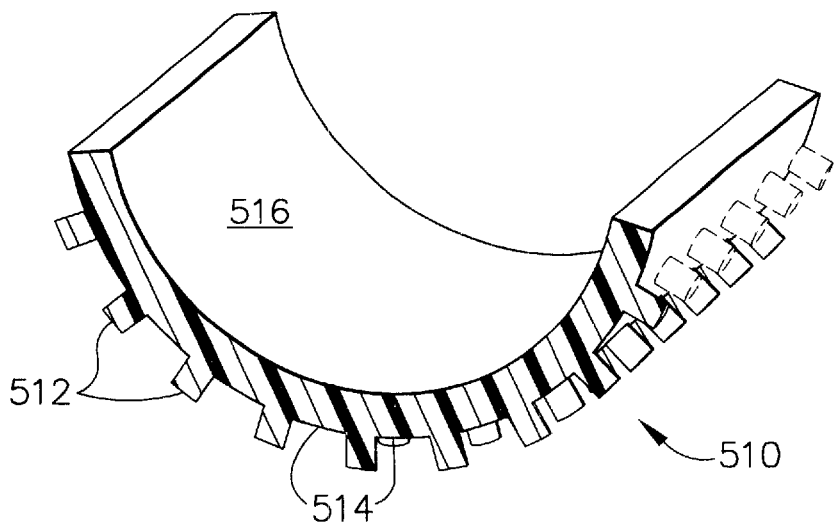

In FIG. 16B, the two mold plates 500 and 502 are pressed against the flexible mold 156, which itself takes the overall shape of a concave structure (as seen from above in this view). An open chamber at 504 is thereby created between the top microstructure portions of the mold and the bottom surface of the top mold plate 500. A hole 506 in the top mold plate 500 can be used to place fluidic material (such as a molten plastic or a prepolymer material) into this chamber 504.

The chamber 504 is now filled with a prepolymer material, such as polyurethane (PU), epoxy, polymethyl methacrylate (PMMA), bone suturing materials, dental polymers, or other similar prepolymer compound. Once the prepolymer material is in place, it is cured as appropriate, using heat energy or perhaps electromagnetic energy, such as ultraviolet light or visible light (one of the mold halves would have to be transparent to the particular wavelength if curing via light). This is the configuration viewed in FIG. 16C.

Once cured, the mold plates 500 and 502 are separated to release the cured polymer material, which has now become a convex microneedle array 510. The individual microneedles are designated by the reference numeral 512, while the semicircular substrate surface between microneedles is designated by the reference number 514. The "inner" surface 516 of the substrate is essentially concave, and could be used to form a reservoir to hold a liquid, if desired.

Figure 16E:
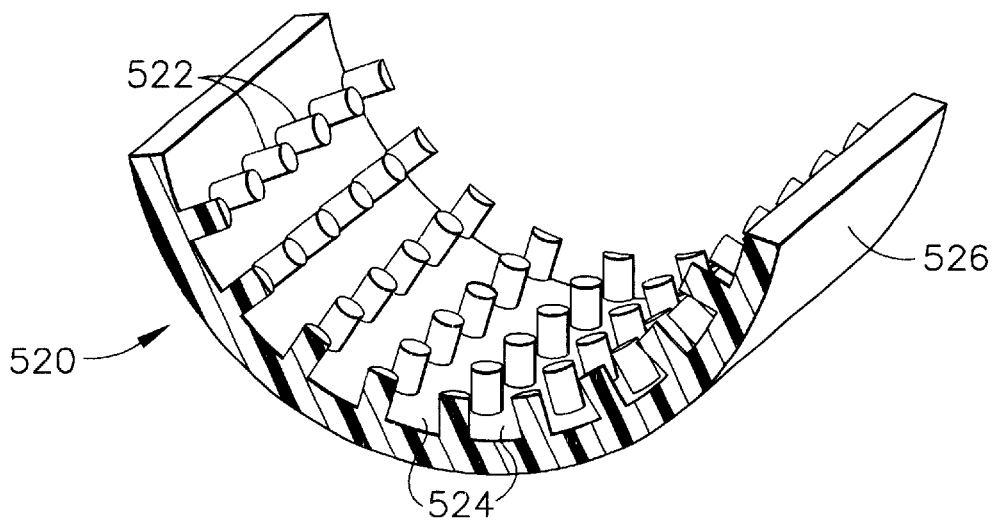

If the mold plates 500 and 502 are made in the opposite shapes—i.e., if the top mold plate 500 was made in a concave shape and the bottom mold plate was made in a convex shape—then the resulting microneedle array would also be in the opposite shape, i.e., an overall concave shape. This results in a microneedle array 520 that has the appearance as illustrated in FIG. 16E. The individual microneedles are designated by the reference numeral 522, while the semi-circular substrate surface between microneedles is designated by the reference number 524. The "outer" surface 526 of the substrate is essentially convex.

The use of the above flexible mold has many advantages: a single microstructure mold 156 can be used to manufacture microneedle arrays that are of various circular arcuate aspects. For example, two different convex shapes can be manufactured from the single flexible mold 156, simply by using two different angled plates for the top and bottom plates 500 and 502. Of course, concave shaped microneedles can also be made from the same flexible mold 156, by use of two opposite shaped top and bottom plates (not shown).

Polymeric Hollow Microneedles

Figure 12A:
FIGS. 12A–12G are diagrammatic views in cross-section of some of the structural steps employed to fabricate polymeric hollow microneedles by replica molding of multilayer patterns.
Figure 12B:
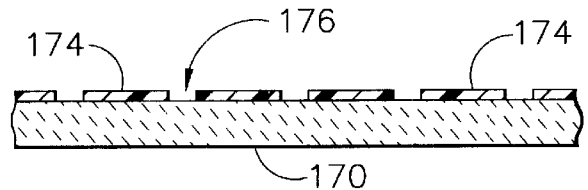

Polymeric hollow microneedles can be fabricated using multilayer photoresist masters, as illustrated in "FIG. 12," which consists of FIGS. 12A–12G. Starting at FIG. 12A, a film 172 of a photoresist material such as SU-8 is spin-coated on a silicon wafer 170, then baked to dryness at about 90° C. The thickness of the photoresist could be in the range of 10–100 microns. This photoresist film 172 is then patterned with cylindrical holes by use of photolithography, thereby resulting in an array of holes having a diameter of about 10–100 microns, as illustrated in FIG. 12B. The holes are represented at the reference numerals 176, while the remaining photoresist film is represented at 174, which bounds these holes 176.

Figure 12C:
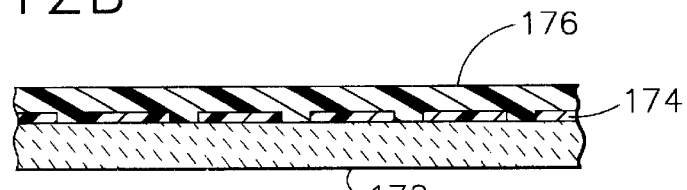

This patterned wafer structure is now coated again with a second layer of photoresist 176, having a thickness of about 10–200 microns, or perhaps thicker if desired, resulting in the structure illustrated in FIG. 12C. The photoresist layer 176 is now patterned with hollow cylinders that are centered on the holes of the bottom layer (originally the film layer 172) using photolithography techniques.

Figure 12D:
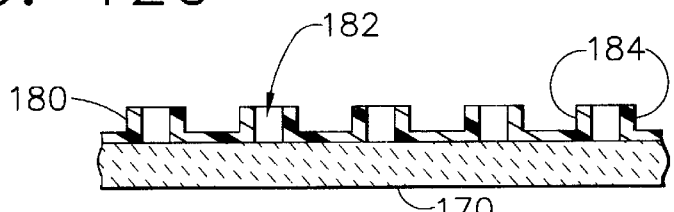

This photoresist structure is now silanized, covered with polydimethylsiloxane (PDMS) under a vacuum, and cured for about two hours in the range of 60–70° C. The resulting structure is illustrated in FIG. 12D, in which the final photoresist material has the form of an array of hollow microneedles, and given the overall designation 180. Each of the microneedles has an outer cylindrical wall at 184, which encompasses a hollow cylindrical volume 182.

Figure 12E:
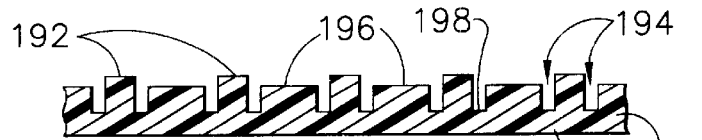

The PDMS material 180 is detached from the silicon/photoresist master at room temperature, and now becomes a mold itself, which is filled with a prepolymer such as polyurethane (PU), epoxy, polymethyl methacrylate (PMMA), bone suturing materials, or dental polymers. This now has the form of the structure 190 on FIG. 12E. As can be seen in FIG. 12E, cylindrical "posts" at 192 are formed, which are surrounded by open areas 194, which become a mold replica for forming microneedles that are hollow and cylindrical. The PDMS mold replica also has relatively flat surfaces at 196 that will become the substrate substantially flat surfaces between microneedle positions, and also has a final "bottom" surface (as viewed on FIG. 12E) at 198 that represents the deepest portion of the cylindrical open areas 194.

Figure 12F:
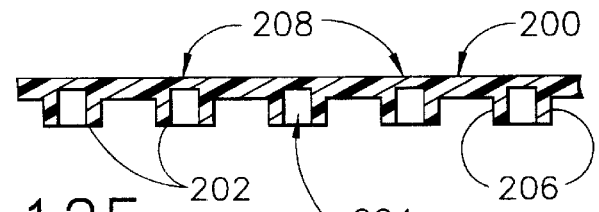
Figure 12G:
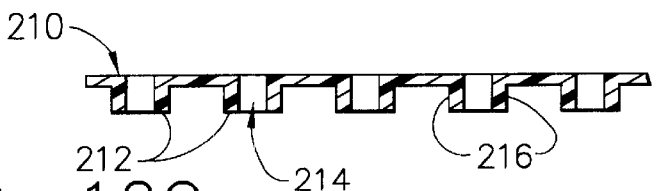
Figure 12H:
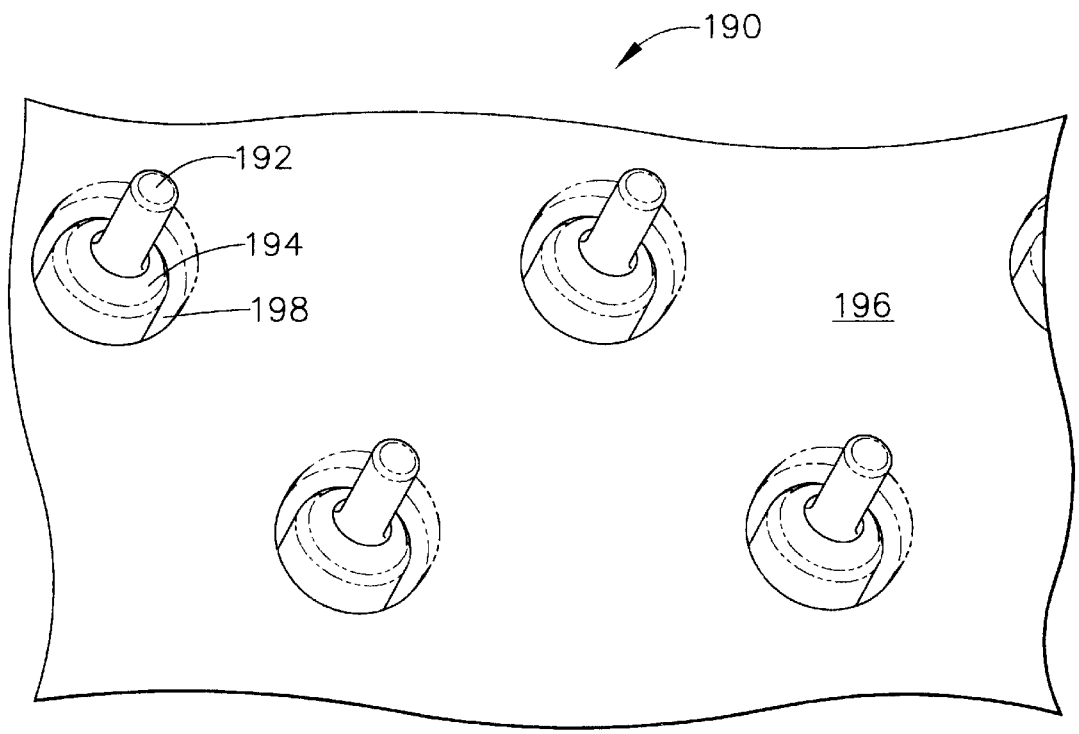
FIG. 12H is a perspective view of a PDMS replica molding, as seen in FIG. 12E.

FIG. 12H provides a perspective view of this structure 190, in which the relatively flat surface 196 represents the largest surface area as seen in this view. The cylindrical posts that protrude the farthest are designated at the reference numerals 192, which have the cylindrical outer channels 194 with a bottom surface at 198.

An embossing polymer is now placed on top of this surface, which will become the actual microneedle structure after the embossing procedure has been completed. In general, the embossing polymer would be squeezed against the PDMS mold replica 190, although that may not be necessary in certain applications or by use of certain materials. This results in a microneedle array structure 200, as illustrated in FIG. 12F.

As an alternative to embossing, a prepolymer material could be placed against the replica mold structure 190 and cured as appropriate (e.g., by use of heat energy or electromagnetic energy, such as visible light or ultraviolet light) in a soft lithography process; and after curing the microneedle array is separated from the mold 190. This also results in a microneedle array structure 200, as illustrated in FIG. 12F.

The microneedle array structure 200 consists of multiple microneedle structures 202, each having a cylindrical wall at 206, which encompasses a cylindrical volumetric space at 204. These microneedles are "closed" at this point, and take the overall form of "microcups." The closed end portion of the microneedles is formed by the surface 208 of the array structure 200.

Since it may be desired to create hollow microneedles that have through-holes, the closed portion 208 can be removed from the array structure, which then provides the structure 210 illustrated on FIG. 12G. These hollow microneedles or microtubes are indicated at the reference numeral 212, and have outer cylindrical walls 216 which encompass a through-hole of an open cylindrical shape at 214.

If the embossing procedure is to be used with a PDMS mold, such as that described above, then the softening point of the polymer to be embossed should be less than about 400° C. to avoid any significant deformation of the PDMS microstructures of the mold piece 190. Of course, if the mold was instead made of a metallic material, then a much higher temperature embossing procedure and material could be used.

Figure 12I:
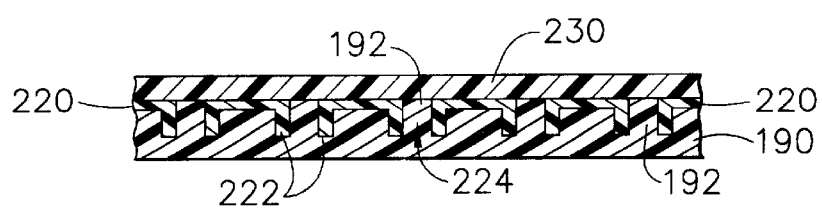
FIGS. 12I–12J are further diagrammatic views in cross-section of some of the structural steps employed to fabricate polymeric hollow microneedles by replica molding of multilayer patterns.

The mold structure 190 on FIG. 12E can also be used to directly create hollow microneedles without the need for a milling or grinding procedure to remove the closed portion 208, as seen on FIG. 12F. Referring now to FIG. 12I, the surface of the mold structure 190 is covered with an embossing polymer material at 220, and is squeezed under pressure by a top plate (or top mold half) 230. The embossing polymer material is allowed to harden or cure before the top mold half 230 is removed. Hollow cylindrical structures are thereby formed in the embossing polymer material 220, in which the walls of the cylinders are indicated at 222, and the internal openings at 224.

Figure 12J:
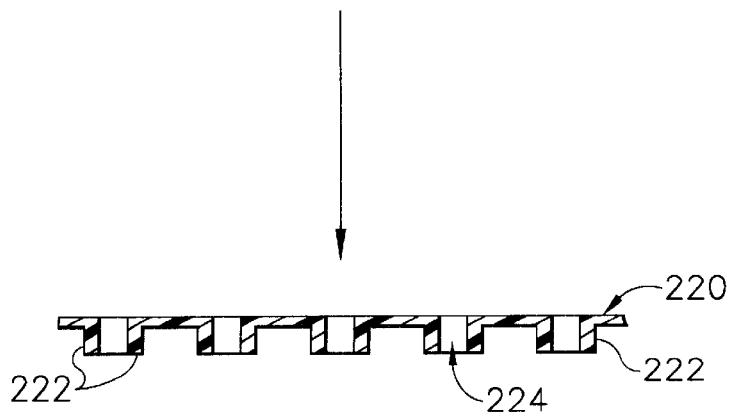

FIG. 12J illustrates the molded material after the top mold half 230 is removed. The new structure 220 continues to exhibit cylindrical openings which are now through-holes at 224, each such hole having a cylindrical wall structure at 222. The holes 224 were directly formed during the molding process because the top mold half 230 removed all excess embossable material from the top of the posts 192 of the mold structure 190 (see FIG. 12I).

It will be understood that the through-holes and associated wall structures could have a shape other than cylindrical without departing from the principles of the present invention. Certainly these hollow microneedles formed in the microneedle array structure 220 instead could be elliptical, square, rectangular, or edged in form.

Electrochemical Sensors Inside Microneedles

Macroscale glucose electrochemical sensors consisting of two electrodes immersed in a conducting media composed of glucose oxidase, electrolytes, and hydrogel are among the most reliable sugar detectors available. In such systems, glucose oxidase converts sugar to carbon dioxide and hydrogen, and an electrical signal is generated by the catalytic oxidation of hydrogen on the surface of a platinum electrode. Microneedle devices that include electrodes can be used as electrochemical sensors, and also they can be used for iontophoretic or electrophoretic delivery of drugs in interstitial fluids. Fabrication techniques to create electrodes that are integrated with the microneedle devices is described in detail below. Procedures for the construction of such microelectrodes on the surface of metallic or polymeric microneedles is disclosed using vapor deposition techniques.

Figure 13A:
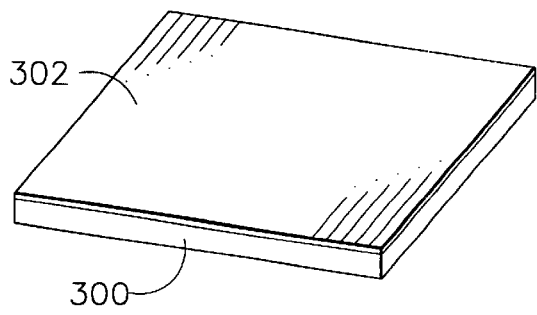
FIGS. 13A–13C, 13F–13I, are perspective views of some of the structural steps used to construct electrodes inside hollow microneedles.
Figure 13F:
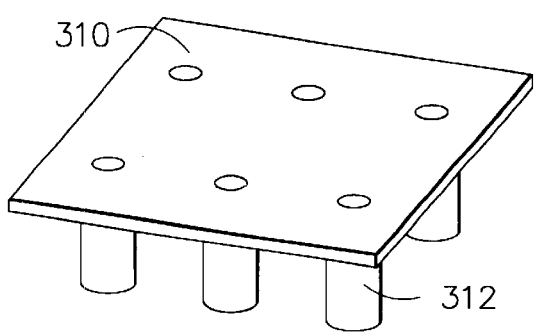
Figure 13B:
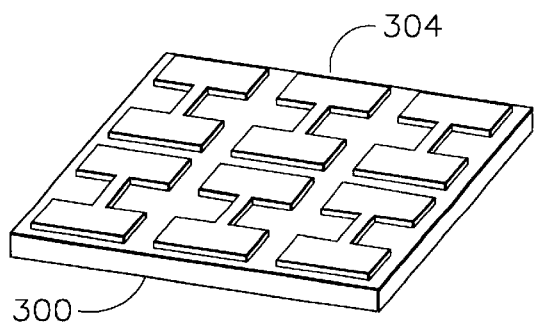
Figure 13G:
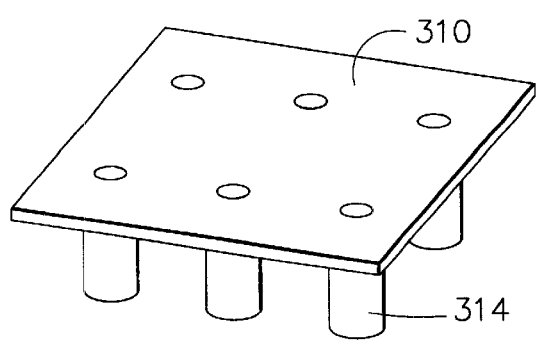
Figure 13C:
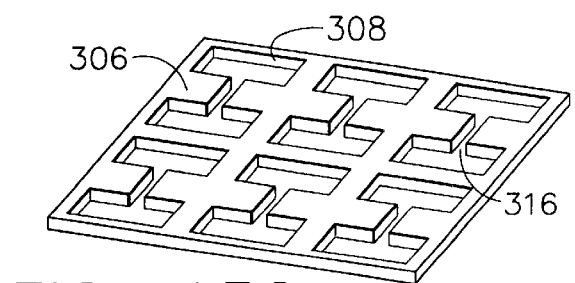
Figure 13I:
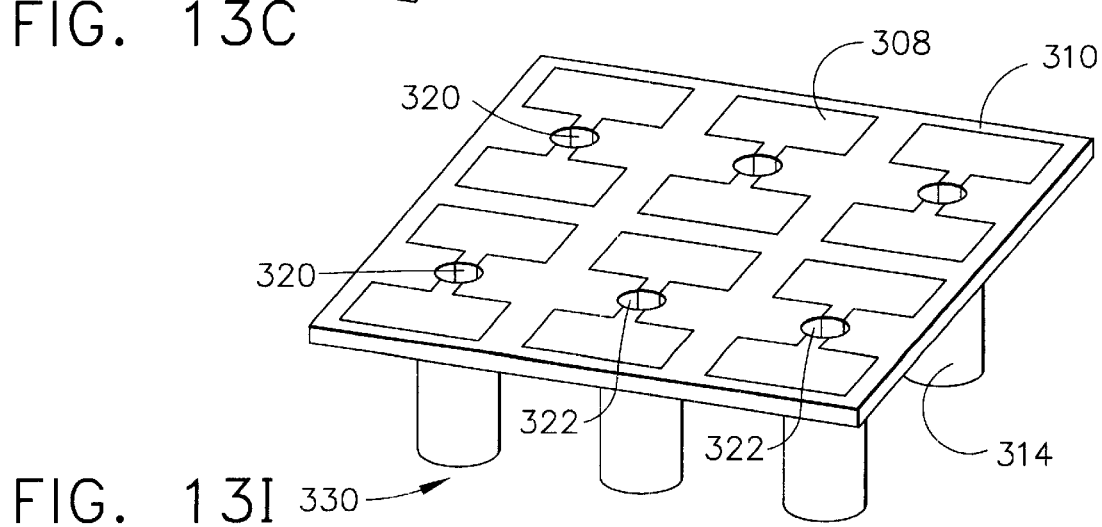
Figure 13E:
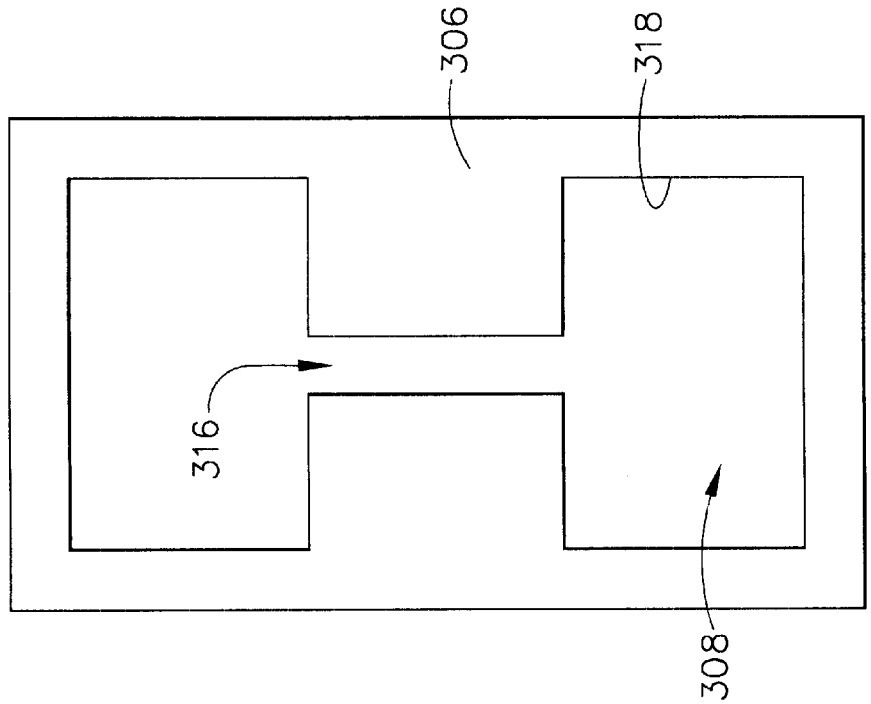
FIGS. 13D–13E are magnified plan views of the individual electrode patterns used in the photolithography steps of FIGS. 13B and 13C.
Figure 13D:
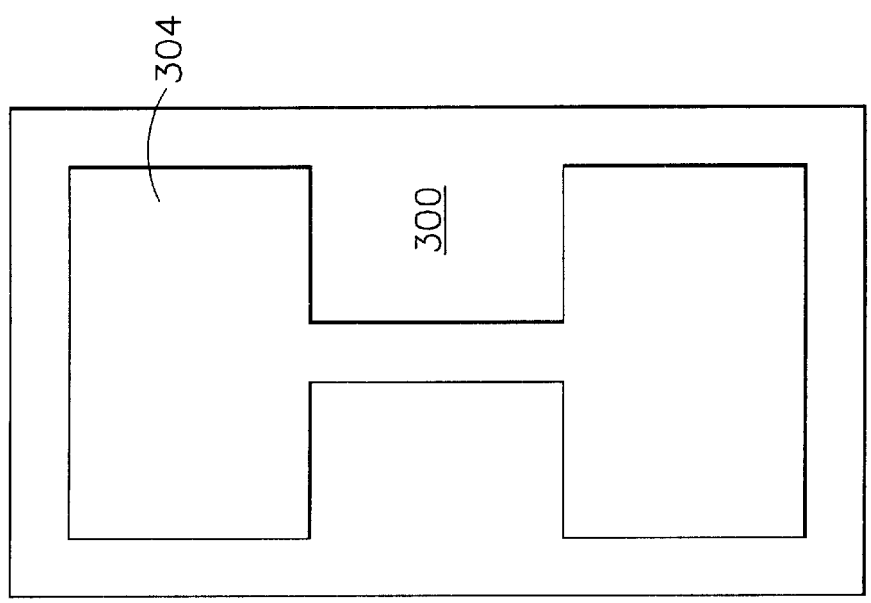
Figure 13H:
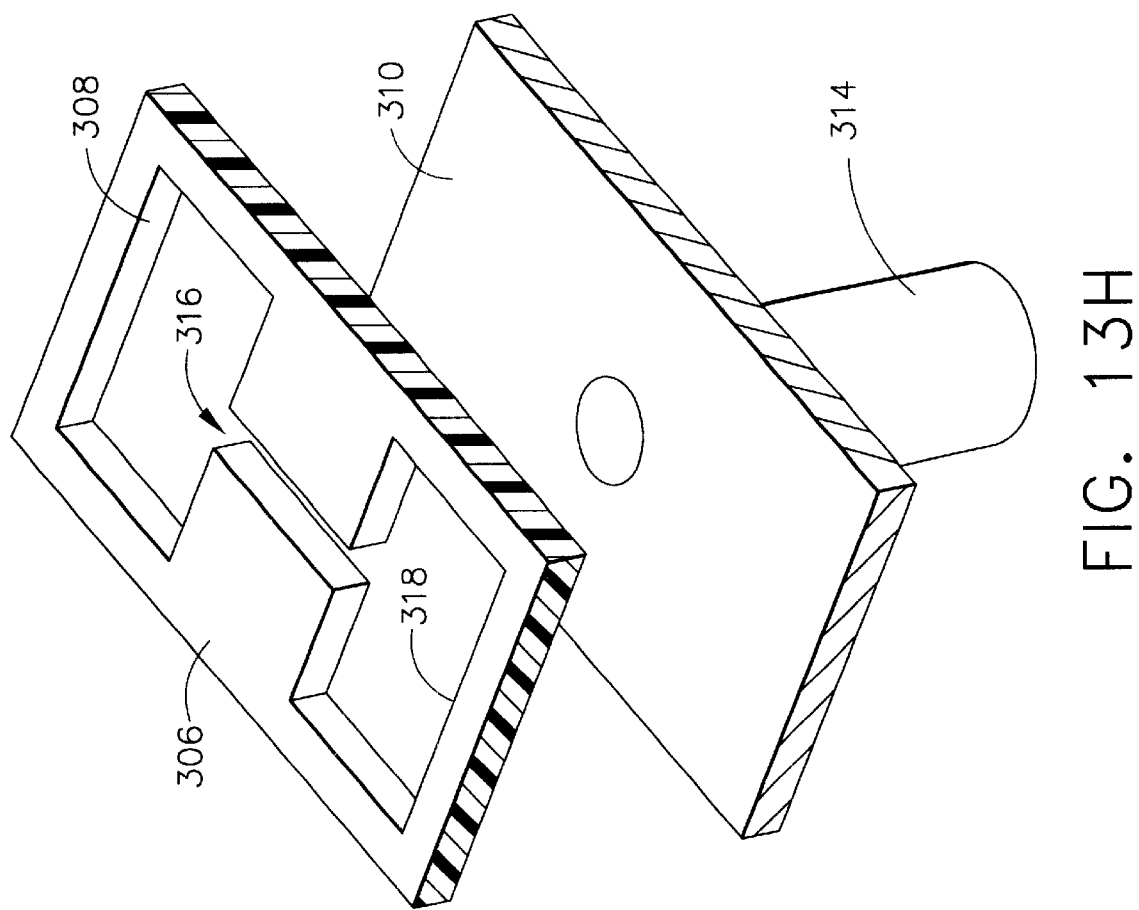

"FIG. 13" illustrates the fabrication processes and structural designs of such microelectrodes in microneedle structures, and consists of FIGS. 13A–13J. In FIG. 13A, a silicon wafer 300 has a spin-coating of photoresist 302, which could be SU-8 photoresist having a thickness of approximately 50 microns. The photoresist is patterned with a structure illustrated in FIG. 13D. One specific design is illustrated in FIG. 13D, in which the photoresist at 304 has dimensions provided on FIG. 13, and which appears on FIG. 13B as an array of such patterned designs.

This patterning procedure preferably involves photolithography, after which the structure is silanized. After that has occurred, the patterned wafer is covered with PDMS, pressed against a flat surface such as a glass slide, then cured at about 60° C. in a soft lithography process step. The PDMS membrane is illustrated in FIG. 13C after it has been removed from the wafer, and is designated generally by the reference numeral 306. A single structure having this shape is illustrated in FIG. 13E, in which the PDMS membrane 306 has an open area of a shape as illustrated at 308.

The structure 306 represents holes or openings 308 in the PDMS membrane that will be used as a mask during a metal vapor deposition procedure. The longitudinal portion 316 of this opening 308, in the relative center area of the pattern, is designed to form two microelectrodes inside each microneedle. The larger rectangular segments 318 of the pattern 308 are utilized to construct electrically conductive pads 304 that will connect the microelectrodes to leads of an electrochemical analyzer. When using the dimensions illustrated on FIG. 13D, each of the pads 304 will have dimensions of about 300 microns×700 microns, and the longitudinal portion is represented by a rectangular shape 316 having dimensions of about 25 microns by 300 microns.

An array 310 of polymeric or metallic microneedles is prepared, and forms a structure as illustrated in FIG. 13F, by which microneedles 312 protrude from one surface of the array structure or substrate 310. If the microneedles are metallic, they can be prepared using the fabrication techniques as described in reference to either FIG. 9 or 10. If metallic microneedles are utilized, a thin film (of approximately 5–10 microns in thickness) of an insulating polymer is electroplated on the surfaces of this array 310, thereby providing a structure as illustrated in FIG. 13G which is coated by an insulative layer of material. This will lead to a layer of insulative coating at 314 on the microneedles themselves. Of course, if the microneedle array structure 310 consists of an insulative material, then no additional polymer layer is required.

The cured PDMS pattern 306 is now placed upon the planar face of the microneedle structure 310 and the linear or longitudinal center portions 316 of each of the patterns 308 are aligned with each of the microneedle structures 314. This involves the PDMS layer 306 being placed against the top surface of the microneedle array 310, as viewed in FIG. 13H. Once that has occurred, a metal vapor deposition procedure can commence, while the structures are held in place by some type of clamp, tape, or temporary adhesive.

A layer of metal, such as gold or platinum, is then vapor deposited on the membrane/microneedle structure in a thermal evaporator, after which the PDMS mask 306 is detached from the microneedles, thereby forming a microneedle array structure 330, as illustrated in FIG. 13I. While in the thermal evaporator, the samples are held at about 30–45° C. with respect to the metal source to ensure the deposition of metal inside the microneedles. The needles are filled with the conducting media described above (e.g., hydrogel, electrolytes, or glucose oxidase) before they are used as glucose sensors. Each of the resulting microneedles 314 protrudes from the planar substrate 310, and each of these hollow microneedles 314 includes an electrode structure 320 that runs at least part way down the inside cylindrical wall surface 322 of the microneedles 314. The electrode structure 320 is electrically connected to a pad 306, as illustrated in FIG. 13I.

Figure 13J:
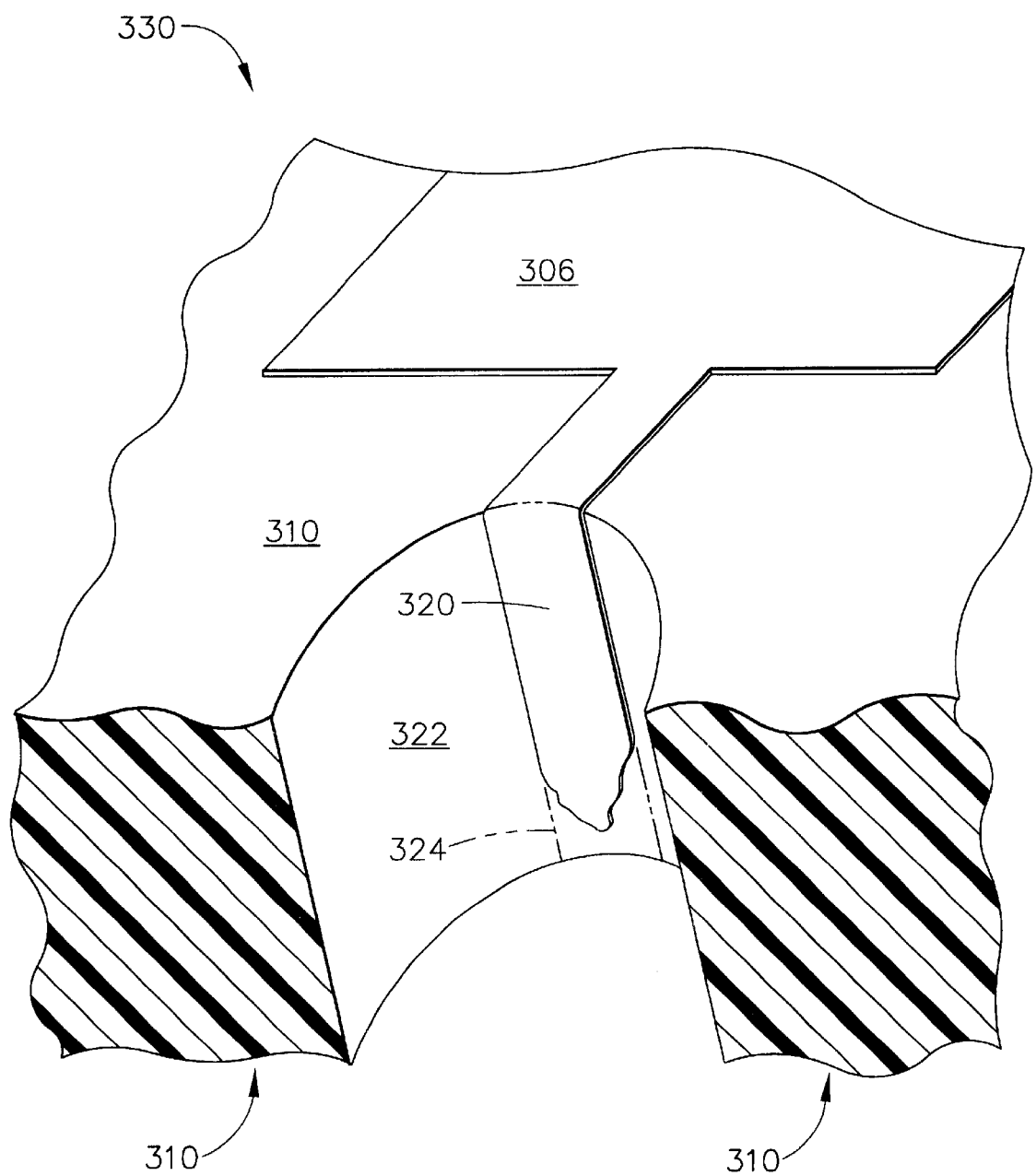
FIG. 13J is a perspective view in partial cross-section and magnified of a single hollow microneedle having an internal electrode, as seen in FIG. 13I.

A more detailed view of this structure 330 is provided in FIG. 13J, by which the microneedle array 330 includes an upper planar surface or substrate 310, an electrically conductive pad 306, an electrode 320 that is both connected to the pad 306 and runs down the inside surface of the cylindrical wall 322 that forms the inner hollow surface of the microneedle itself.

The fabrication of a PDMS mask and the vapor deposition of metallic material is not necessary if the polymer to be electroplated is a photoresist. In this situation, the electrodes and pads can be constructed by use of photolithography techniques. Not only are very small electrode structures able to be constructed by photolithography, but in addition larger electrode structures can be formed, also using photolithography. Such an example is illustrated in FIG. 14.

Figure 14:
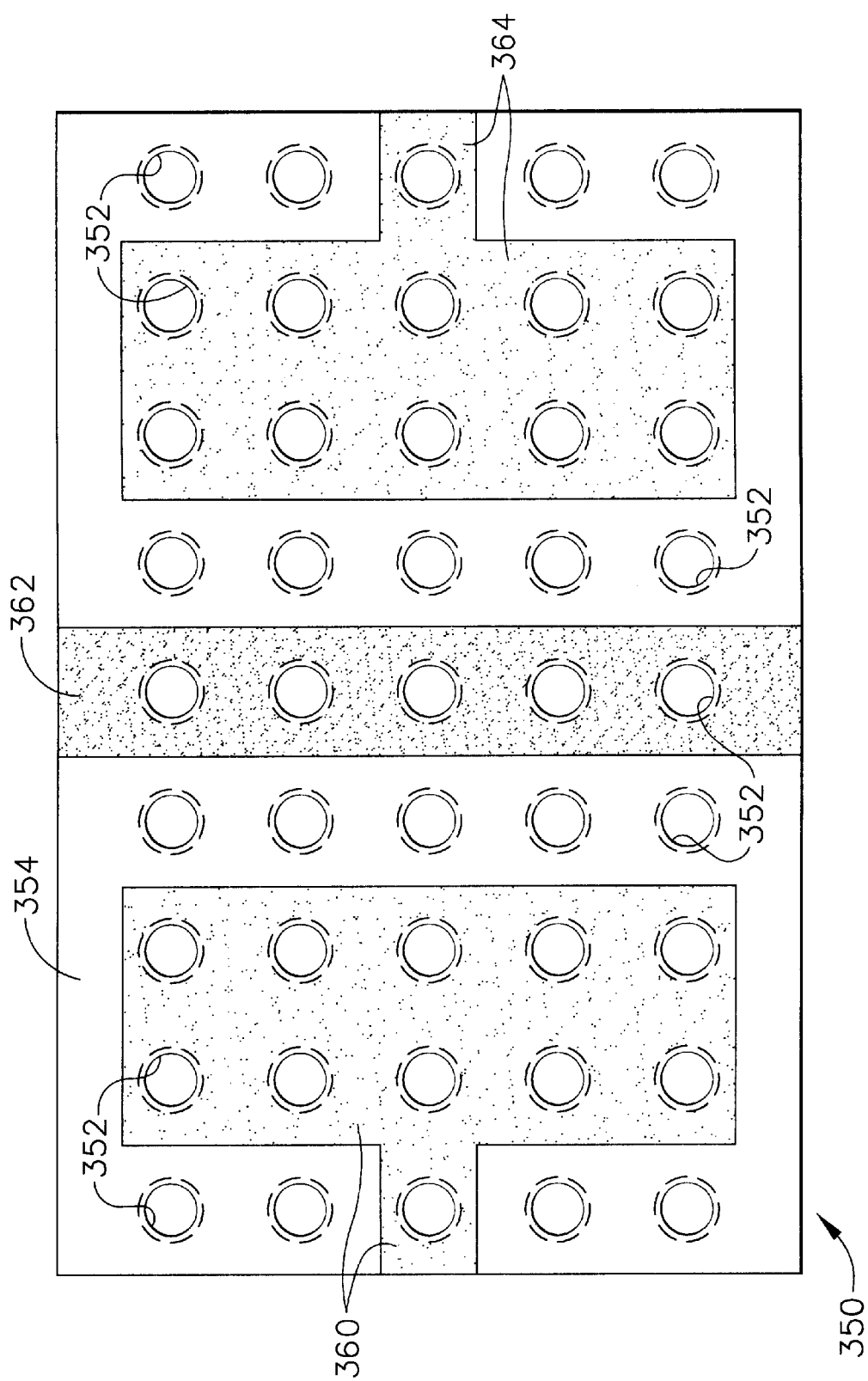
FIG. 14 is a plan view of a microneedle array that contains electrode bands.

In FIG. 14, electrode "bands" are formed on a microneedle array structure, rather than using independent electrode systems for each microneedle as illustrated in FIG. 13I. In FIG. 14, a large number of microneedles 352 are formed on a microneedle array 350. The top planar surface 354 shows that different materials can be applied thereto. For example, a "working electrode" 360 can be formed on one portion of this structure 350, and can encompass a number of the microneedles 352, including the inner cylindrical hollow surfaces of these microneedles 352. A "counter electrode" 364 can be formed in a different area, and can also encompass many such microneedle structures 352. Finally, a "reference electrode" 362 can be formed using a third set of microneedles 352. Each electrode area is electrically conductive between each of its individual microneedles 352 by an electrically conductive metallic surface along the top of the substrate at 354. Such electrode bands could alternatively be formed on the opposite side of the microneedle array. In other words, electrode bands could be formed on either the top or the bottom of the microneedle array 350 when hollow microneedles are used.

On the other hand, solid microneedles could be used at 352, if desired. In that circumstance, the solid structure 352 could have the form of cylindrical posts that are coated by electrically conductive metal within the various bands 360, 362, or 364. If the microneedles started as hollow structures, their inner diameters could be filled (or at least plugged) by the metal of the electrode bands 360, 362, or 364.

Glucose sensors could also be formed using polymeric microneedles, as mentioned above. The polymeric microneedles can be formed in the same manner as metallic microneedles, in which the initial specimen is covered with a PDMS mask prepared as described in reference to FIGS. 13A–13C. The electrodes can then be formed by metal vapor deposition in a thermal evaporator, or perhaps in a sputtering machine.

Figure 15A:
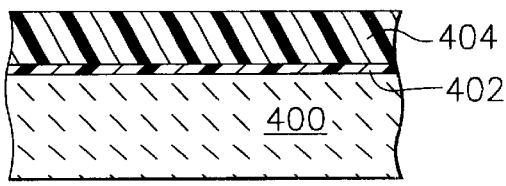
FIGS. 15A–15L are diagrammatic cross-sectional views of structural steps used to fabricate sharp tipped microneedles.
Figure 15B:
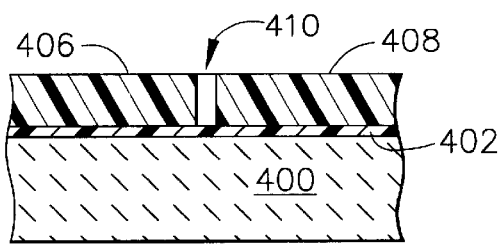

Using the principles of the present invention, it is also possible to make a mold insert that can create a microneedle having a sharp tip using photolithography techniques. "FIG. 15" illustrates some of the fabrication steps in such a procedure, in which "FIG. 15" consists of FIGS. 15A–15L. Starting with a silicon wafer 400 that has a top layer 402 of either PDMS material or silicon oxide material, the wafer structure is coated with a layer of photoresist 404. This layer 404 is baked to dryness and then patterned using a transparency mask and an electromagnetic light source (such as an ultraviolet light source) so as to create locally a relatively small cylindrical hole, as seen at 410 in FIG. 15B. In FIG. 15B, the photoresist layer 404 is now shown as two halves, at 406 and 408.

Figure 15C:
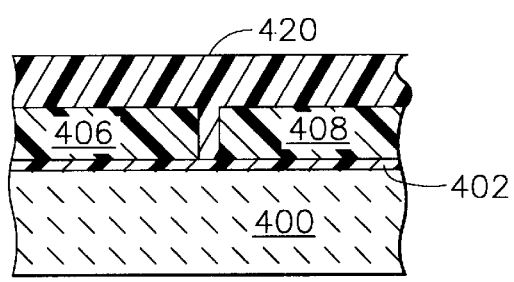
Figure 15D:
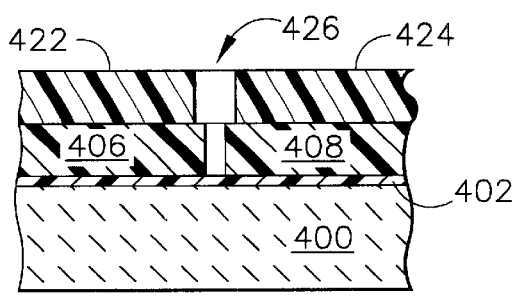

After this first photolithography step, a second layer of photoresist material 420 is now placed atop the structure, as viewed in FIG. 15C. After this photoresist 420 has been baked to dryness, it is patterned using ultraviolet light and a transparency mask to create locally another cylindrical opening that is somewhat larger than the first one 410. This second cylindrical opening is designated by the reference numeral 426 on FIG. 15D, and it can be seen as separating the photoresist material 420 into two halves, 422 and 424. It will be understood that this FIG. 15D is a cut-away view, and the opening 426 is actually the further half (from the observer) of a cylindrical inner wall, and therefore, the two "halves" 422 and 424 still make up a single layer of photoresist material that has certain openings, such as the one at 426.

Figure 15E:
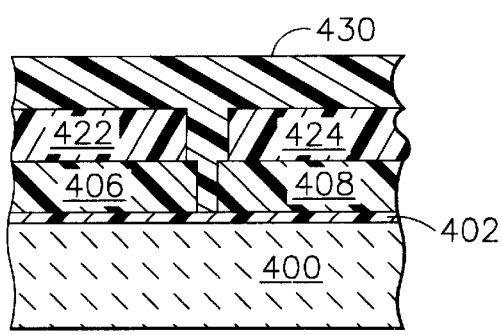
Figure 15F:
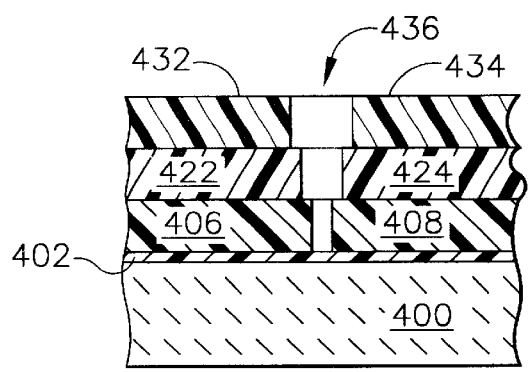

The next step after this second photolithography step is to again place a further layer of photoresist material 430 atop the structure, thereby arriving at the structure illustrated on FIG. 15E. After this new layer of photoresist at 430 has been baked to dryness, it is patterned using a light source and a transparency mask to create locally a somewhat larger cylindrical hole, as seen at 436 on FIG. 15F. The photoresist layer 430 is now illustrated as consisting of two halves at 432 and 434, which are indeed a single layer.

Figure 15G:
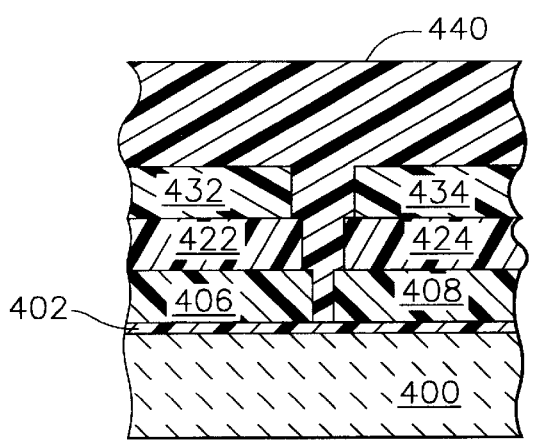

After this third photolithography step, still another layer of photoresist material 440 is placed atop this structure, as viewed in FIG. 15G. In this example, the photoresist layer 440 is much thicker than any of the earlier photoresist layers 404, 420, or 430.

Figure 15H:
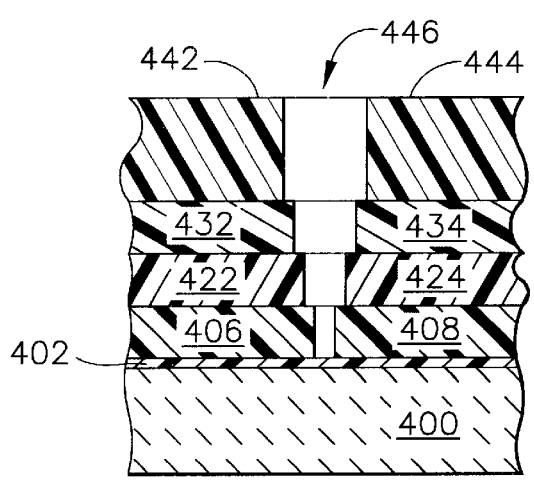

After the photoresist layer 440 has been baked to dryness, it is patterned using ultraviolet light and a transparency mask to create locally a still larger cylindrical hole, as seen at 446 on FIG. 15H. The photoresist layer 440 is now shown in two halves at 442 and 444. It will be understood that certainly more than three intermediate layers of photoresist material could be used to create a mold form, as compared to that shown in FIG. 15H.

Figure 15I:
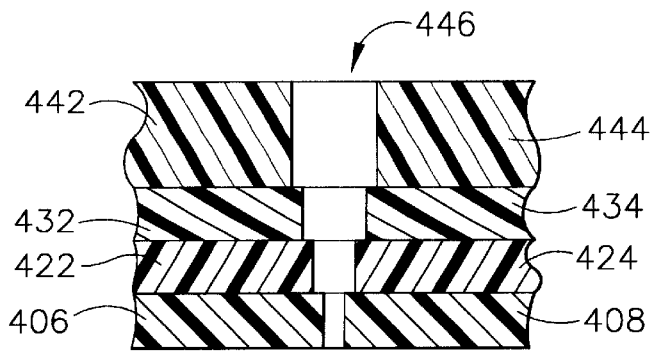

In FIG. 15I, the mold structure, generally designated by the reference numeral 450, has been separated from the silicon wafer 400 by dissolving or otherwise decomposing the sacrificial layer 402 with an appropriate reagent. As noted above, PDMS can be decomposed with TBAF, and silicon oxide or silicon dioxide can be immersed in hydrofluoric acid to cause the detachment.

Figure 15J:
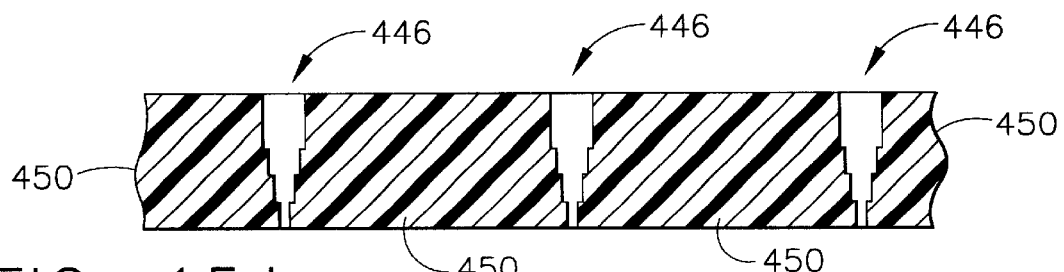

FIG. 15J shows several of the holes 446 as part of an array of such holes in the total mold structure 450. Certainly, for any practical microneedle array mold, there would be dozens if not hundreds or thousands of such holes 446 as part of the mold structure 450 in its entirety.

Figure 15K:
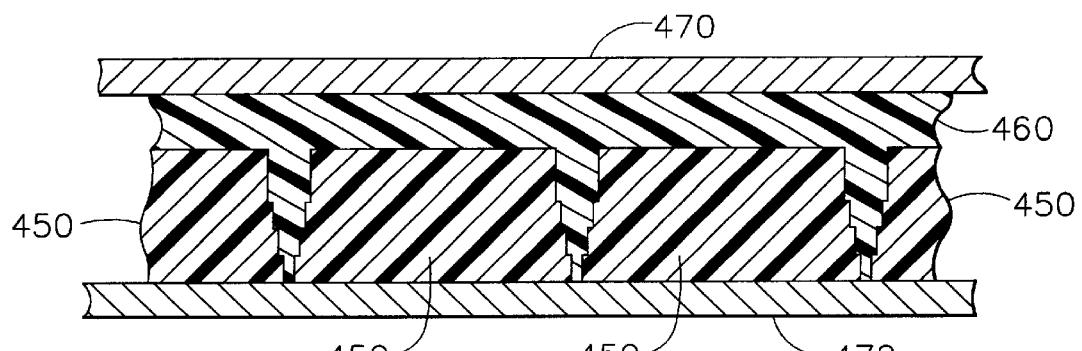
Figure 15L:
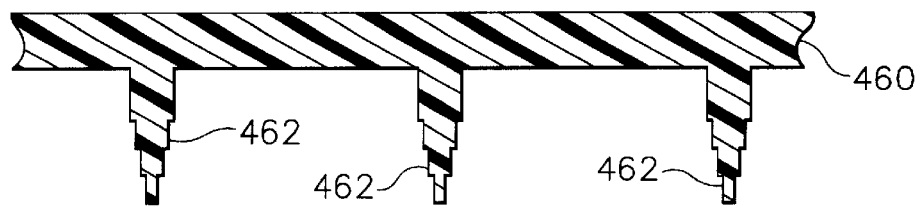

Now that the mold 450 has been fabricated, microneedles can be formed by use of injection molding, embossing, or some other type of microfabrication technique, even including microcasting if it is desirable to create metallic microneedles (although different materials would have to be used). FIG. 15K shows an arrangement where a plastic structure generally designated at the reference numeral 460 is placed between two mold halves 470 and 472, which act as pressure bases, and also retain the plastic material 460 within the mold cavities that are available in contact with the patterned mold 450. As can be seen in FIG. 15K, the plastic material 460 will flow into the shaped holes 446 that were created in this mold structure 450. Once detached from the mold, an array of microneedles is formed, generally designated by the reference numeral 460. Array 460 includes multiple "sharp" microneedles 462, as viewed in FIG. 15L. As noted above, these "sharp tip" microneedles could be of various sizes and shapes, and certainly could be created from more than three stages of photoresist layers being patterned by use of photolithography techniques, without departing from the principles of the present invention.

One optional variant in the microneedles described above is to create a structure in which the base material is different from the microneedle structure material, which allows the designer freedom to create hydrophobic-hydrophilic combinations. Examples of such different types of materials are as follows: glass, mica, Teflon®, and metalized surfaces.

It will be understood that all of the microneedle structures described above can be of any length or width, or any inner diameter for hollow microneedles or microcups, without departing from the principles of the present invention. Certain exemplary dimensions have been disclosed above, but these are only examples of prototypical units. It will also be understood that the microneedles (both solid and hollow) could be constructed of various shapes other than cylinders, such as elliptical profiles, or "edged" microneedles, such as disclosed in a patent application that is assigned to The Procter & Gamble Company, under Ser. No. 09/580,780) which was filed on May 26, 2000, and titled "Intracutaneous Edged Microneedle Apparatus." This patent application is incorporated herein by reference in its entirety.

It will be further understood that the chemical compounds disclosed above are exemplary for certain prototypical microneedles, and as such are quite useful, but at the same time other compounds might easily be employed without departing from the principles of the present invention. For example, the substrate does not always need to be silicon, and the sacrificial layer is not always required to be either PDMS or silicon oxide. Certainly other polymers or plastics could be used than disclosed above, or other metals.

Another alternative embodiment of the microneedle structures described above is to change their properties by a "surface modification" treatment which allows a coating to occur at the molecular level. To effect this treatment, the silicon needles can be silanized with reagents to derivatize the surfaces. Typically, such coating would occur after the microneedles are already formed.

Yet another alternative embodiment would be a plasma treatment of epoxy or other types of polymeric microneedles to impart different surface properties. Again, such treatment would typically occur after the microneedles have been formed. One such different surface properties could be to impart hydrophobic/hydrophilic properties to the microneedles.

Still another alternative embodiment of the microneedles of the present invention is to incorporate carbon fibers or other composite materials into epoxy or polymeric needles and perhaps the substrate. The use of harder materials could reinforce the polymeric needles and make them more rigid. One example would be to add carbon fibers or composite materials into a photoresist compound, such as that illustrated in FIG. 3A at 34. This would lead to the microneedles at the microneedle array 40 in FIG. 3D to be more rigid. The entire microneedle structure could be hardened, if desired, by incorporating carbon fibers or other composite materials into all of the materials used to manufacture the structure, including the base or substrate.

As an alternative to the above, the substrate materials utilized in creating the microneedles of the present invention could be made more flexible, although it normally would be preferred to keep the microneedles themselves as a rigid structure. One methodology for creating substrates that are more flexible is to add microchannels and grooves to the substrate, thereby making the fairly rigid material have some "bendability" while not being prone to fracture.

Another alternative "flexible" embodiment is to create more flexible microneedles themselves, in which the microneedle structures would be sufficiently rigid to break the skin, but still have some flexibility that would be quite useful for continuous sensing and dispensing systems. This would be the opposite of the break-away microneedles disclosed above, for example in FIGS. 8B and 8C. These flexible microneedles would be achieved by using materials such as elastomers and polyurethanes that are moldable or embossable. Examples of such elastomers are silicones.

Yet another alternative "flexible" embodiment is to create a microneedle structure in which the entire structure is at least somewhat flexible, although the flexibility properties of the needles could be different than the flexibility properties of the base. An example of this is where the needles, or at least their tips, are made of a first material (having a first flexibility or elasticity property) and the base/substrate is made of a second material (having a second flexibility or elasticity property). For example, the base/substrate could be made of nylon while the microneedles are made of silicone or polyurethane, thereby providing a microneedle array that has a barely flexible base/substrate but a much more flexible set of needles.

A further alternative embodiment for the microneedles of the present invention is to place a final outer layer of a metal coating over the microneedle structures. For solid microneedles, this would have the appearance as viewed in FIG. 9E, which illustrates plated metal over a PDMS replica that itself could become a microneedle array. Such a structure has the advantage of fairly quick manufacturing, while remaining accurate at the microstructure level and while having the surface properties of a structure formed entirely from metal. The thickness of the outer metal coating can be controlled by a vapor deposition or electroplating process.

Several different processes can be used to coat microstructures with metal layers. The most common techniques are electroplating (or electrodeposition), electroless plating, sputtering, vapor deposition, and plasma deposition. In an electroplating process, a conductive sample is used as the cathode (or the anode for electrooxidation reactions) of an electrochemical system that contains ions of the metal that will be deposited on the substrate (e.g., Ni, Cu, Ag, Au, Pb, Sn, Al or Pt).

It is also possible to electroplate some alloys (e.g., Pb/Sn, bronze, or steel), metal oxides (e.g., titanium or aluminum oxides), and polymers (e.g., polyphenols or polypyrroles). Depending on the material that is electroplated, the plating solution can be aqueous (e.g., Ni, Cu, Ag, Au, Pb, Sn, or Pt) or organic (e.g., polymers, Al, or titanium oxides) and may contain stabilizers, brighteners, and wetting agents. In many instances, electroplating allows the formation of crystalline films as thick as 1–2 millimeters. If the sample to be electroplated is not electrically conductive, it must be coated with a thin film of a conductive material (e.g. metals or conductive polymers) prior to immersion in the electrochemical cell.

Electroless plating can be used to deposit metal, oxides, or polymers on virtually any kind of substrates. In this case, the sample is cleaned using organic solvents (e.g., acetone or methanol) and/or mineral acids (e.g., hydrofluoric or nitric acid), activated for metal deposition using a metallization catalyst (e.g., palladium chloride), and immersed in a solution including electron donor species (e.g., phosphate ions) and the material that is going to be plated. The thickness of the electroless plated films can range from a several angstroms to a few millimeters and is affected by the pH of the plating solution, time of reaction, and concentration of the chemicals involved in the deposition process.

Sputtering can only be used to deposit thin metal films (from angstroms to nanometers) on either conductive or non-conductive substrates. In the sputtering instrument, gas ions (e.g., Ar) are used to vaporize the atoms of a metal source (e.g., Au, Pt, Cr, Ag, or Cu) that are then directed towards the sample surface for deposition using an electric field. Sputtering is a fast (e.g., taking only a few minutes) and inexpensive technique that is convenient to coat non-conductive samples with seed metal layers for a later step of electroplating, including the fabrication of microelectrodes (employing a mask, such as the mask 306 in FIG. 13H), provided that there is good adhesion between the metal film and the substrate.

Vapor deposition is preferred over sputtering in the cases where microsmooth metal and oxide films are desired (having a coating thickness on the order of angstroms or nanometers) or when common metals (e.g., Au, Ag, Al, or Cu) do not adhere strongly to the substrates. For vapor deposition, the sample are placed in a vacuum chamber where the metals are evaporated using resistive heating or an electron beam. The metal vapors deposit on the cold areas of the vacuum chamber, including the sample surface. Usually, the specimens are coated with a few angstroms of a metal adhesion layer (e.g., Cr or Ti) prior to the deposition of the metal or oxide or interest. This process is generally completed in one or two hours and is employed for the fabrication of electrodes, seed layers for electroplating processes, and the deposition of thin layers of metal on three dimensional samples (in which the sample can be rotated at an angle in the vacuum chamber).

Plasma deposition is a technique that can be employed to deposit very thin films (having a thickness in the order of angstroms) of several kinds of materials (e.g., organic compounds, polymers, oxides, or metal precursors) on conductive or non-conductive substrates. This process is slow and expensive. It is normally utilized to prepare films of materials that cannot be handled using the methodologies mentioned above.

External Channel Microneedles

Figure 17:
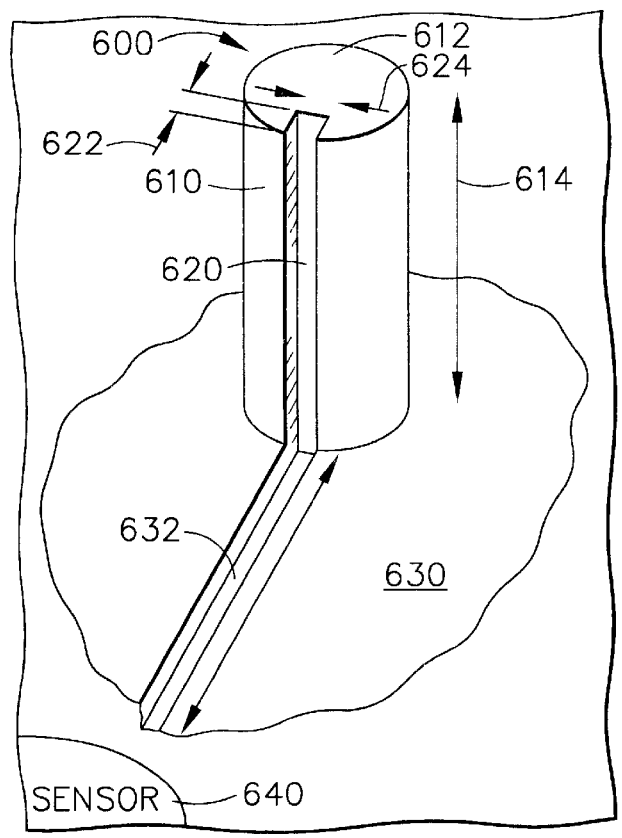
FIG. 17 is a perspective view of a solid microneedle having an external channel along its elongated side wall.

Solid microneedles can be manufactured with external channels running along one or more sides of the elongated walls. For example, FIG. 17 illustrates a solid microneedle 600 that has a elongated side wall 610 and a top surface 612 at its tip. The length of the microneedle is designated by the dimension line 614, which could be in the range of 100–500 microns.

An external channel 620 is formed in one side of the wall 610. The channel 620 is substantially rectangular in profile in this view, and could have dimensions (at 622 and 624, respectively) of about 10 microns by 10 microns. Of course, the channel 620 could be of other dimensions, if desired. Channels can also be made to taper so as to increase capillary driving forces.

The external channel 620 is preferably in communication with another channel 632 that is in the base structure 630 of the microneedle array. This base channel 632 could be used to transport interstitial fluid, for example, to a sensor device 640. This sensor device could be electrochemical or optical in nature, or perhaps could use a different principle of operation.

Groups of solid microneedles having external channels could be formed of a single microneedle array. On FIG. 18, four such solid microneedles are illustrated at the reference numerals 650, 652, 654, and 656. Their corresponding external channels are designated by the reference numerals 660, 662, 664, and 666, respectively. Note that each microneedle has two such external channels on FIG. 18.

Figure 18:
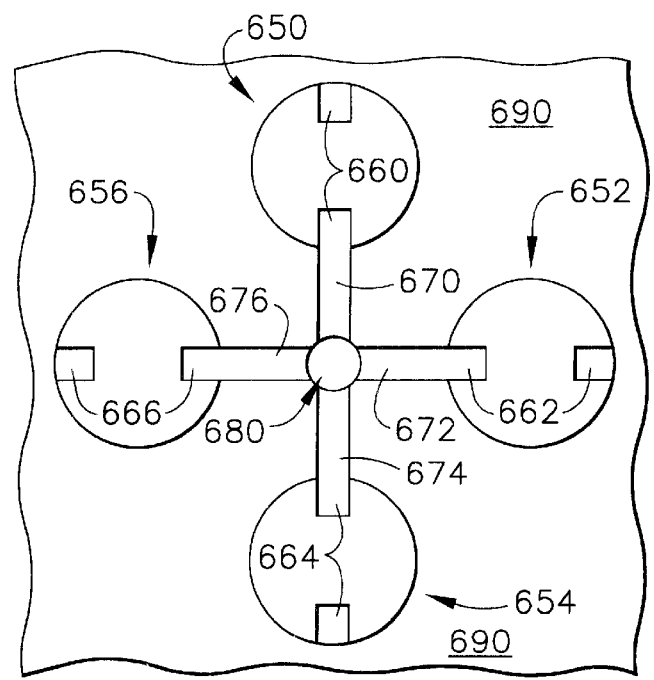
FIG. 18 is a top, elevational view of multiple solid microneedles each having two external channels along their elongated side wall.

Some of the external channels are fluidically joined by channels in the base structure 690. These base channels are designated by the reference numerals 670, 672, 674, and 676, respectively. All four of the base channels 670, 672, 674, and 676 meet at a "collection port" 680, which could be a through-hole in the microneedle base structure (or substrate) 690. Such collection ports could be located anywhere on the base 690, and the illustrated embodiment of FIG. 18 is merely an exemplary situation where four such microneedles are grouped to a single collection port. Moreover, there could be an individual collection port per microneedle, if desired; such paired microneedles and collection ports would typically be located proximal to one another.

The fluid that traverses the base channels 670, 672, 674, and 676 and external microneedle channels 660, 662, 664, and 666 could be traveling in either direction. If sampling interstitial fluid, for example, then the collection ports would likely lead to a chamber or reservoir that will either have an associated sensing apparatus, or will trap the fluid for later use or measurement. If dispensing a fluid, for example, the collection ports would be in fluidic communication with a reservoir that contains the drug or active that is to be placed through the outer skin layer.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed:

1. A method for fabricating microneedles, said method comprising:
   (a) providing a substrate that includes a plurality of microstructures;
   (b) coating said substrate with a layer of a first moldable material that takes the negative form of said plurality of microstructures, and hardening said first moldable material;

(c) separating said hardened first moldable material from said substrate, thereby creating a micromold from said hardened first moldable material containing said plurality of microstructures; and (d) applying a second moldable material onto said micromold, allowing said second moldable material to harden using a soft lithography procedure, then separating said hardened second moldable material from said micromold, thereby creating a microneedle structure from said hardened second moldable material having the three-dimensional negative form of said plurality of microstructures of the patterned micromold;

wherein said microneedle structure comprises one of: (a) a plurality of solid protrusions, (b) a plurality of hollow protrusions forming through-holes, (c) a plurality of hollow protrusions forming microcups that do not extend entirely through said hardened second moldable material, or (d) a plurality of solid protrusions, each having at least one surface external channel.

2. The method as recited in claim 1, wherein said first moldable material comprises PDMS, said second moldable material comprises a prepolymer, and said substrate comprises one of silicon or a metallic substance; and wherein said microneedle structure comprises a polymeric material.

3. The method as recited in claim 1, wherein said substrate is constructed by: beginning with a wafer material, coating said wafer material with at least one layer of a photoresist material, and patterning said photoresist material with a plurality of microstructures by use of a photolithography procedure, such that said patterned photoresist material comprises said plurality of microstructures; and wherein said first moldable material is processed and hardened by a second soft lithography procedure.

4. The method as recited in claim 3, wherein said wafer comprises silicon, said photoresist material comprises SU-8, said first moldable material comprises PDMS, and said second moldable material comprises a prepolymer; and wherein said microneedle structure comprises a polymeric material.

5. A method for fabricating microneedles, said method comprising:

(a) providing a substrate that includes a plurality of microstructures;

(b) coating said substrate with a layer of a first moldable material that takes the negative form of said plurality of microstructures, and hardening said first moldable material;

(c) separating said hardened first moldable material from said substrate, thereby creating a micromold from said hardened first moldable material containing said plurality of microstructures;

(d) applying a second moldable material onto said micromold, allowing said second moldable material to harden using a soft lithography procedure, then separating said hardened second moldable material from said micromold, thereby creating a microneedle structure from said hardened second moldable material having the three-dimensional negative form of said plurality of microstructures of the patterned micromold;

(e) providing a second substrate that includes a second plurality of microstructures, wherein said second plurality of microstructures is substantially complementary in shape as compared to said first plurality of microstructures;

(f) coating said second substrate with a layer of a third moldable material that takes the negative form of said second plurality of microstructures, and hardening said third moldable material;

(g) separating said hardened third moldable material from said second substrate, thereby creating a second micromold from said hardened third moldable material containing said second plurality of microstructures;

(h) applying a fourth moldable material onto said second micromold, allowing said fourth moldable material to harden using a soft lithography procedure, then separating said hardened fourth moldable material from said second micromold, thereby creating a second microneedle structure from said hardened fourth moldable material having the three-dimensional negative form of said second plurality of microstructures of the patterned second micromold; and (i) applying a layer of a fifth moldable material upon one of said first or second microneedle structures, placing said first and second microneedle structure into a face-to-face relationship to thereby sandwich said layer of fifth moldable material therebetween, allowing said layer of fifth moldable material to harden using a soft lithography procedure, then separating said hardened fifth moldable material from both said first and second microneedle structures, thereby creating a third microneedle structure from said hardened fifth moldable material having the three-dimensional negative form of both said first and second microneedle structures.

6. The method as recited in claim 5, wherein said first and third moldable materials comprise PDMS, said second and fourth moldable materials comprise a prepolymer, said substrate comprises one of silicon or a metallic substance, and said fifth moldable material comprises a prepolymer; and wherein said first, second, and third microneedle structures each comprises a polymeric material.

7. A method for fabricating microneedles, said method comprising:

(a) providing a substrate that includes a plurality of microstructures;

(b) coating said substrate with a layer of a first moldable material that takes the negative form of said plurality of microstructures, and hardening said first moldable material;

(c) separating said hardened first moldable material from said substrate, thereby creating a micromold from said hardened first moldable material containing said plurality of microstructures; and (d) applying a second moldable material onto said micromold, allowing said second moldable material to harden using a soft lithography procedure, then separating said hardened second moldable material from said micromold, thereby creating a microneedle structure from said hardened second moldable material having the three-dimensional negative form of said plurality of microstructures of the patterned micromold;

wherein said first moldable material after hardening exhibits a flexibility characteristic and, therefore, can be deformed to a predetermined extent without breaking; and further comprising: after creating said micromold from said hardened, flexible first moldable material, deforming said micromold during the step of applying the second moldable material onto said micromold, thereby creating either a concave or convex micromold.

* * * * *

UNITED STATES PATENT AND TRADEMARK OFFICE
CERTIFICATE OF CORRECTION

PATENT NO. : 6,663,820 B2
DATED : December 16, 2003
INVENTOR(S) : Arias et al.

It is certified that error appears in the above-identified patent and that said Letters Patent is hereby corrected as shown below:

Column 13,
Line 38, delete "bum" and substitute therefor -- burn --.

Column 21,
Line 38, delete "121" and substitute therefor -- 12I --.

Column 23,
Lines 7, 19 and 38, delete "131" and substitute therefor -- 13I --

Column 24,
Line 56, delete "151" and substitute therefor -- 15I --.

Signed and Sealed this

Twenty-eighth Day of June, 2005

JON W. DUDAS
*Director of the United States Patent and Trademark Office*